US011384367B2

(12) United States Patent
Gladden et al.

(10) Patent No.: US 11,384,367 B2
(45) Date of Patent: Jul. 12, 2022

(54) SYNTHESIS OF BIOPRODUCTS FROM LIGNIN-DERIVED AROMATICS BY GENETICALLY MODIFIED MICROORGANISMS

(71) Applicants: THE REGENTS OF THE UNIVERSITY OF CALIFORNIA, Oakland, CA (US); NATIONAL TECHNOLOGY & ENGINEERING SOLUTIONS OF SANDIA, LLC, Albuquerque, NM (US); BATTELLE MEMORIAL INSTITUTE (FOR MANAGEMENT AND OPERATION OF PACIFIC NORTHWEST NATIONAL LABORATORY), Richland, WA (US)

(72) Inventors: John M. Gladden, Alameda, CA (US); Jeffrey M. Skerker, Berkeley, CA (US); Jay D. Keasling, Berkeley, CA (US); James Kirby, Berkeley, CA (US); Junko Yaegashi, Hacienda Heights, CA (US)

(73) Assignees: THE REGENTS OF THE UNIVERSITY OF CALIFORNIA, Oakland, CA (US); NATIONAL TECHNOLOGY AND ENGINEERING SOLUTIONS OF SANDIA, LLC, Albuquerque, NM (US); BATTELLE MEMORIAL INSTITUTE (FOR MANAGEMENT AND OPERATION OF PACIFIC NORTHWEST NATIONAL LABORATORY), Richland, WA (US)

( * ) Notice: Subject to any disclaimer, the term of this patent is extended or adjusted under 35 U.S.C. 154(b) by 0 days.

(21) Appl. No.: 16/450,824

(22) Filed: Jun. 24, 2019

(65) Prior Publication Data

US 2019/0330663 A1 Oct. 31, 2019

Related U.S. Application Data

(63) Continuation of application No. PCT/US2017/067737, filed on Dec. 20, 2017.

(60) Provisional application No. 62/438,434, filed on Dec. 22, 2016.

(51) Int. Cl.
| | | |
|---|---|---|
| *C12P 1/02* | (2006.01) | |
| *C07G 1/00* | (2011.01) | |
| *C08H 7/00* | (2011.01) | |

(52) U.S. Cl.
CPC ............. *C12P 1/02* (2013.01); *C07G 1/00* (2013.01); *C08H 6/00* (2013.01)

(58) Field of Classification Search
CPC ...... C12P 1/02; C07G 1/00; C08H 6/00; C08H 8/00
See application file for complete search history.

(56) References Cited

U.S. PATENT DOCUMENTS

| | | | |
|---|---|---|---|
| 5,959,167 A | 9/1999 | Shabtai et al. | |
| 8,535,916 B2 | 9/2013 | Del Caqrdayre et al. | |
| 9,765,044 B2 | 9/2017 | Socha et al. | |
| 2014/0163142 A1* | 6/2014 | Zhang | C08L 97/005 524/14 |
| 2016/0017381 A1* | 1/2016 | Beckham | C12P 7/44 562/592 |
| 2016/0312257 A1* | 10/2016 | Noguera | C12N 9/001 |
| 2017/0247729 A1 | 8/2017 | Liszka et al. | |
| 2017/0369918 A1 | 12/2017 | Sun et al. | |
| 2018/0371502 A1* | 12/2018 | Beckham | C10L 1/02 |

FOREIGN PATENT DOCUMENTS

| | | |
|---|---|---|
| ES | WO2017178686 A1 | 10/2017 |
| WO | WO2016070125 A1 | 5/2016 |
| WO | WO2016105538 A1 | 6/2016 |
| WO | WO2016154631 A1 | 9/2016 |

OTHER PUBLICATIONS

Chang-Zhou Chen et al., "Structural Characterization of Lignin Extracted with Alkaline Hydrogen Peroxide from Furfural Residue," 49 Cellulose Chem. Technol. 153 (2015).*
International Preliminary Report on Patentability for Int'l Appl. PCTUS2017067737, Gladden et al, dated Jul. 4, 2019.
International Search Report/Written Opinion for PCT/US2017/067737, Gladden et al, dated Mar. 13, 2018.
Apel et al., Evolved hexose transporter enhances xylose uptake and glucose/xylose co-utilization in *Saccharomyces cerevisiae*. Scientific Reports (2016), 6.
Beckham et al, Opportunities and challenges in biological lignin, Current Opinion in Biotechnology (2016) vol. 42:50-53.
Villar et al, Oxidation of hardwood kraft-ignin to phenolic derivatives with oxygen as oxidant. Wood Science and Technology (2001). 35: 245-255.
Salvachua et al, Towards Lignin Consolidated Bioprocessing: Simultaneous lignin depolymerization and product generation by bacteria, Green Chemistry (2015).DOI: 10.1039/c5gc01165e.

(Continued)

*Primary Examiner* — Nicholas E Hill
(74) *Attorney, Agent, or Firm* — Robin C. Chiang; Lawrence Berkeley National Laboratory

(57) ABSTRACT

The present invention provides for a method of converting a depolymerized lignin aromatic compound into a bioproduct, comprising: (a) providing a composition comprising a depolymerized lignin aromatic compound, optionally a depolymerized cellulose, and optionally a depolymerized hemicellulose, and (b) introducing a genetically modified microorganism to the composition, wherein the genetically modified microorganism is capable of converting the depolymerized lignin aromatic compound into a bioproduct; such that the depolymerized lignin aromatic compound is converted into a bioproduct.

23 Claims, 8 Drawing Sheets

(56) References Cited

OTHER PUBLICATIONS

Yaegashi et al, Rhodosporidium toruloides: a new platform organism for conversion of lignocellulose into terpene biofulels and bioproducts. Biotechnology for Biofuels (2017) 10:241. DOI: 10.1186/s13068-017-0927-5.
Clark et al, Green chemistry and the biorefinery: a partnership for a sustainable future. Green Chemistry (2006) 8, 853-860.
Himmel et al, Biomass recalcitrance: engineering plants and enzymes for biofuels production. Science (2007). vol. 315, Issue 5813, 804-807.
Ragauskas et al., Lignin valorization: improving lignin processing in the biorefinery. Science (2014). vol. 344, Issue 6185, 1246843.
Zaldivar et al., Fuel ethanol production from lignocellulose: a challenge for metabolic engineering and process integration. Appl. Microbiol Biotechnol (2001). 56: 17-34.
Wiebe et al., Lipid production in batch and fed-batch cultures of Rhodosporidium toruloides from 5 and 6 carbon carbohydrates. BMC Biotechnology (2012), 12:26.
Zhu et al., A multi-omic map of the lipid-producing yeast Rhodosporidium toruloides. Nature Communications (2012).
Ageitos et al., Oily yeasts as oleaginous cell factories. Applied Microbiology and Biotechnology (2011). 90, 1219-1227.
Zhang et al., Engineering Rhodosporidium toruloides for increased lipid production. Biotechnol Bioeng (2016). 113, 1056-1066.
Lin et al., Functional integration of multiple genes into the genome of the oleaginous yeast *Rhodosporidium toruloides*. Fems Yeast Research (2014). 14, 547-555.
Liu et al., Characterization of glyceraldehyde-3-phosphate dehydrogenase gene RtGPD1 and development of genetic transformation method by dominant selection in oleaginous yeast *Rhodosporidium toruloides*. Applied Microbiology and Biotechnology (2013). 97, 719-729.
Koh et al, Molecular characterization of KU70 and KU80 homologues and exploitation of a KU70-deficient mutant for improving gene deletion frequency in Rhodosporidium toruloides. Bmc Microbiology (2014). 14-50.
Xu et al., Transforming biomass conversion with ionic liquids: process intensification and the development of a high-gravity, one-pot process for the production of cellulosic ethanol. Energy & Environmental Science (2016). 9, 1042-1049.
Sun et al., CO2 enabled process integration for the production of cellulosic ethanol using bionic liquids. Energy & Environmental Science (2016), 2822-2834.
Maimone et al., Modem synthetic efforts toward biologically active terpenes. Nature Chemical Biology (2007), 3, 396-407.
Ro et al., Production of the antimalarial drug precursor artemisinic acid in engineered yeast. Nature (2006). 440, 940-943.
Peralta-Yahya et al., Identification and microbial production of a terpene-based advanced biofuel. Nature Communications (2011), 2.
Tyo et al., Stabilized gene duplication enables long-term selection-free heterologous pathway expression. Nature Biotechnology (2009), 27, 760-U115.
Yin et al., Effects of chromosomal gene copy number and locations on polyhydroxyalkanoate synthesis by *Escherichia coli* and *Halomonas* sp. Applied Microbiology and Biotechnology (2015), 99, 5523-5534.

Paradise et al., Redirection of flux through the FPP branch-point in *Saccharomyces cerevisiae* by down-regulating squalene synthase. Biotechnol Bioeng (2008), 100, 371-378.
Kirby et al., Use of Nonionic Surfactants for Improvement of Terpene Production in *Saccharomyces cerevisiae*. Applied and Environmental Microbiology (2014), 80, 6685-6693.
Pandey et al., Lignin Depolymerization and Conversion:A Review of Thermochemical Methods. Chem. Eng. Technol. (2011), 34, 1: 29-41.
Groff et al., Supplementation of Intracellular XylR Leads to Coutilization of Hemicellulose Sugars. Applied and Environmental Microbiology (2012) 78, 2221-2229.
Li et al., Comparing the Recalcitrance of Eucalyptus, Pine, and Switchgrass Using Ionic Liquid and Dilute Acid Pretreatments. Bioenergy Research (2013), 6, 14-23.
Shi et al., Impact of Pretreatment Technologies on Saccharification and Isopentenol Fermentation of Mixed Lignocellulosic Feedstocks. Bioenergy Research (2015), 8, 1004-1013.
Singh et al., Comparison of different biomass pretreatment techniques and their impact on chemistry and structure. Front. Energy Res. (2015), 2.
Liszka et al., Switchable ionic liquids based on di-carboxylic acids for one-pot conversion of biomass to an advanced biofuel. Green Chem (2016), 18, 4012-4021.
Fillet et al., Fatty alcohols production by oleaginous yeast. Journal of Industrial Microbiology & Biotechnology (2015), 42, 1463-1472.
Buzzini et al., Carotenoid profiles of yeasts belonging to the genera *Rhodotorula, Rhodosporidium, Sporobolomyces*, and *Sporidiobolus*. Canadian Journal of Microbiology (2007), 53, 1024-1031.
Ham et al., Design, implementation and practice of JBEI-ICE: an open source biological part registry platform and tools. Nucleic Acids Research (2012), 40.
Abbott et al., Overcoming recalcitrant transformation and gene manipulation in Pucciniomycotina yeasts. Applied Microbiology and Biotechnology (2013), 97,283-295.
Ozaydin et al., Carotenoid-based phenotypic screen of the yeast deletion collection reveals new genes with roles in isoprenoid production. Metab Eng (2013), 15, 174-183.
Sitepu et al., Oleaginous yeasts for biodiesel: current and future trends in biology and production. Biotechnol Adv ((2014), 32, 1336-1360.
Lee et al., Metabolomic profiling of Rhodosporidium toruloides grown on glycerol for carotenoid production during different growth phases. J Agric Food Chem (2014), 62, 10203-10209.
Park et al., Research cellulose crystallinity index: measurement techniques and their impact on interpreting cellulase performance. Biotechnol Biofuels (2010), 3.
Mansikkamaki et al., Structural changes of cellulose crystallites induced by mercerisation in different solvent systems; determined by powder X-ray diffraction method. Cellulose (2005), 12, 233-242.
Pearl, Irwin A. Vanillin from lignin materials. J Am Chem Soc (1942). 64 (6): 1429-1431.
Liu et al., Process of lignin oxidation in an ionic liquid coupled with separation. RSC Advances (2013) 3 (17), 5789-5793.
Kleen et al., Characterization of chemical and mechanical pulps by pyrolysis-gas chromatography / mass spectrometry. J Anal Appl Pyrolysis (1991) 19, 139-151.
Xiang et al., Oxidative Cracking of Precipitated Hardwood Lignin by Hydrogen Peroxide. Appl. Biochem. Biotechnol. (2000) 153. 84-86.

* cited by examiner

SYNTHESIS OF BIOPRODUCTS FROM LIGNIN-DERIVED AROMATICS BY GENETICALLY MODIFIED MICROORGANISMS

CROSS-REFERENCE TO RELATED APPLICATIONS

This application claims priority as a continuation application of PCT International Patent Application No. PCT/US2017/067737, filed Dec. 20, 2017, which claims priority to U.S. Provisional Patent Application Ser. No. 62/438,434, filed on Dec. 22, 2016, both of which are hereby incorporated by reference.

STATEMENT OF GOVERNMENTAL SUPPORT

The invention was made with government support under Contract No. DE-AC02-05CH11231 awarded by the U.S. Department of Energy. The government has certain rights in the invention.

FIELD OF THE INVENTION

The present invention is in the field of converting lignocellulose into a biodiesel or a bioproduct.

BACKGROUND OF THE INVENTION

Growing energy demands and concerns over global warming and environmental pollution associated with the consumption of petroleum have made it imperative to develop and foster a bioeconomy focused on efficient low-carbon emission technologies. Replacement of petroleum-derived fuels and chemicals with bio-based alternatives derived from renewable carbon sources has been identified as a promising approach to help realize a bioeconomy (1). Lignocellulosic biomass, composed primarily of cellulose, hemicellulose and lignin, is the most abundant renewable carbon source available today, and has been widely studied as a substrate for microbial production of bio-based fuels and chemicals. Most of these efforts have focused on converting one or two of the major components of plant biomass, primarily cellulose and hemicellulose, but none of them has demonstrated conversion of all three components by a single microbe into a single non-native bioproduct. Due to its heterogeneity and recalcitrance to depolymerization, the cross-linked phenolic polymer lignin is the most under-utilized of the three components for bioconversion, and is often relegated to being burned for heat and energy generation in a biorefinery (2). However, technoeconomic (TEA) and life-cycle analyses (LCA) have indicated that lignin valorization will be critical for maintaining the economic viability and sustainability of lignocellulosic biorefineries (3).

SUMMARY OF THE INVENTION

The present invention provides for a method of converting a depolymerized lignin aromatic compound into a bioproduct, comprising: (a) providing a composition comprising a depolymerized lignin aromatic compound, optionally a depolymerized cellulose, and optionally a depolymerized hemicellulose, and (b) introducing a genetically modified microorganism to the composition, wherein the genetically modified microorganism is capable of converting the depolymerized lignin aromatic compound into a bioproduct; such that the depolymerized lignin aromatic compound is converted into a bioproduct. The present invention also provides for a composition generated by the introducing step. The present invention also provides for a composition comprising the bioproduct and the composition generated by the introducing step.

The present invention provides for a depolymerized lignin aromatic compound, optionally a depolymerized cellulose, optionally a depolymerized hemicellulose, and a genetically modified microorganism to the composition, wherein the genetically modified microorganism is capable of converting the depolymerized lignin aromatic compound into a bioproduct.

The present invention provides for a mixture of bioproducts produced by converting a mixture of depolymerized lignin aromatic compounds using a genetically modified microorganism capable of converting each depolymerized lignin aromatic compound into a bioproduct.

The mixture of depolymerized lignin aromatic compounds comprises two or more depolymerized lignin compounds described herein.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

These and other objects, advantages, and features of the invention will become apparent to those persons skilled in the art upon reading the details of the invention as more fully described below.

In some embodiments, the depolymerized lignin compound is an aromatic compound, such as p-coumaric acid, conferic acid, or sinapic acid.

Figure 1A:
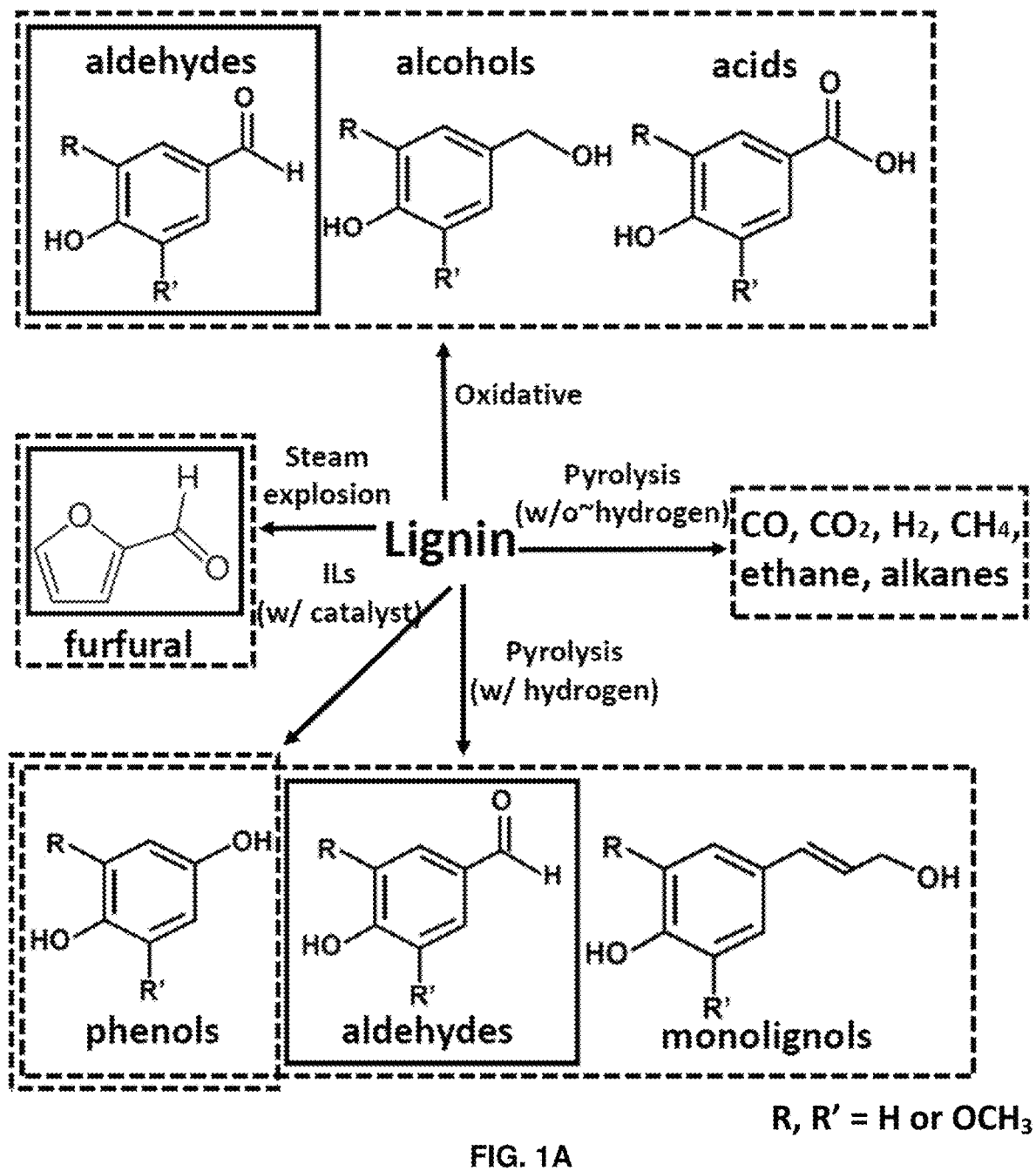
FIG. 1A. Products of various methods for depolymerization of lignins. Dashed boxes represent major products from an indicated method. Aldehydes, alcohols, and carboxylic acids are produced in a variety of traditional (e.g., oxidative, pyrolysis, steam explosion) and emerging (e.g., ionic liquid) methods.

In some embodiments, the composition comprises a mixture of a plurality of classes of or individual depolymerized lignin aromatic compounds. In some embodiments, the composition comprises a two or more classes of or individual depolymerized lignin aromatic compounds. In some embodiments, the composition comprises a three or more classes of or individual depolymerized lignin aromatic compounds. In some embodiments, the composition comprises a four or more classes of or individual depolymerized lignin aromatic compounds. In some embodiments, the composition comprises a five or more classes of or individual depolymerized lignin aromatic compounds. In some embodiments, the composition comprises a ten or more classes of or individual depolymerized lignin aromatic compounds. Exemplary classes of depolymerized lignin aromatic compounds are phenols, aldehydes, alcohols, acids, monolignols, or the like as depicted in FIG. 1A. Exemplary individual depolymerized lignin aromatic compounds are p-coumaric acid, conferic acid, sinapic acid, or the like.

In some embodiments, the composition is resultant mixture of IL-pretreatment of biomass and its depolymerization, wherein the composition comprises a depolymerized lignin compound, a depolymerized cellulose and a depolymerized hemicellulose. Methods to depolymerization are known to the art. Methods of polymerization are taught in PCT International Patent Application Nos. PCT/US2015/000320 and PCT/US2015/058472, and U.S. Provisional Patent Application Ser. No. 62/346,351.

In some embodiments, the genetically modified microorganism is a fungal or bacterial microorganism. In some embodiments, the fungal microorganism is of the genus *Rhodotorula*, *Rhodosporidium*, or *Exophiala*. In some embodiments, the bacterial microorganism is of the genus *Delftia* or *Rhodococcus*.

In some embodiments, the genetically modified microorganism is of one genus selected from the group consisting of *Rhodotorula*, *Rhodosporidium*, *Exophiala*, *Delftia*, and *Rhodococcus*.

In some embodiments, the genetically modified microorganism is of the genus *Rhodotorula*. In some embodiments, the genetically modified microorganism is *Rhodotorula mucilaginosa*, *Rhodotorula graminis*, or *Rhodotorula glutinis*.

In some embodiments, the genetically modified microorganism is of the genus *Rhodosporidium*. In some embodiments, the genetically modified microorganism is *Rhodosporidium toruloides*.

In some embodiments, the genetically modified microorganism is of the genus *Exophiala*. In some embodiments, the genetically modified microorganism is *Exophiala alcalophila*.

In some embodiments, the genetically modified microorganism is of the genus *Delftia*. In some embodiments, the genetically modified microorganism is *Delftia acidovorans*.

In some embodiments, the genetically modified microorganism is of the genus *Rhodococcus*. In some embodiments, the genetically modified microorganism is *Rhodococcus rhodocorus*.

The microorganism is genetically modified to express an enzyme that is heterologous to the microorganism, or to express an enzyme at a higher expression level when compared to the unmodified microorganism, wherein the enzyme converts a depolymerized lignin aromatic compound into another compound, such as a bioproduct.

All are oleaginous except *Exophiala* and *Delftia* and can produce high levels of carotenoids—can be engineered to produce high titers of biodiesel or terpene fuels and bioproducts. Biodiesel can be made chemically by transesterification of TAGs. *Exophiala alcalophila* makes melanin and can be engineered to make high titers of products like tryptophan, folate, serotonin, and salicylic acid. Also, all organisms can convert lignin into ionic liquids, such as choline glutamate. In a lignocellulosic refinery, depolymerized lignin streams can be funneled through one or more of these organisms and converted to additional fuel or non-fuel bioproducts. In some embodiments, the bioproduct is a lignocellulosic biofuel or bioproduct compound. In some embodiments, the bioproduct is bisabolene, bisabolane, amorphadiene, artemisinin, terpene, tryptophan, folate, serotonin, salicylic acid, choline glutamate, or the like.

When the bioproduct is an ionic liquid (IL), the IL can be transferred to the IL-pretreatment saccharification of further biomass to produce further lignin, cellulose, hemicellulose to be depolymerized for introducing to the method of this present invention.

Depolymerized Lignin Aromatic Compounds, and Methods of Producing Thereof

One or more depolymerized lignin aromatic compounds, or a mixture thereof, can be produced in a variety of methods. Such methods are taught in International Patent Application No. WO 2014/172042 and U.S. Pat. No. 9,765,044.

Depolymerized lignin aromatic compounds can be produced by contacting lignin with a depolymerization agent. Depolymerization agents include any chemical or process known in the art for depolymerizing polymeric lignin to low molecular weight compounds (e.g., monomers, dimers, trimers, etc.). In some cases, the depolymerizing agent extracts and depolymerizes the lignin from a lignocellulosic biomass. In other cases, the lignin must be extracted prior to the step of contacting the lignin with a depolymerizing agent. Processes and agents suitable for depolymerizing lignin include those described in, e.g. Pandey, (*Chem. Eng. Technol.*, 34, No. 1, 29-41, 2011); Pearl, (*J Am Chem Soc* 64(6):1429-1431, 1942); Liu, (*RSC Adv* 3(17):5789-5793, 2013); Kleen, (*J. Anal. Appl. Pyrolysis*, 19, 139, 1991); and Xiang, (*Appl. Biochem. Biotechnol.*, 84-86, 153, 2000). Exemplary embodiments of lignin depolymerization methods and examples of low molecular weight compounds thus produced are depicted in FIG. 1A, and include oxidative methods which provide aldehydes, alcohols, and acids; steam explosion which provides the hemicellulose depolymerization and dehydration product furfural or 5-hydroxymethylfurfural; contacting with ionic liquids and a catalyst which provides phenols; and oxidative methods or pyrolysis with hydrogen which provide aldehydes, alcohols, and carboxylic acids.

Depolymerization agents include one or more of ionic liquids or ionic liquid mixtures (including the ionic liquids or ionic liquid mixtures of the invention), hydrogenolysis (e.g., $H_2$ gas, a hydrogen donating agent such as tetralin, sodium formate or formic acid), a dilute acid, a concentrated acid, a base, an oxidizing agent (e.g., nitrobenzene, a metal oxide, hydrogen peroxide, or $O_2$ gas with an appropriate catalyst), Fenton's reagent ($H_2O_2$ and ferrous sulfate), metal organic frameworks of copper or iron, and ammonium hydroxide.

Depolymerization agents can include methods and conditions that provide a high yield of aromatics or a higher yield of aromatics as compared to non-aromatic low molecular weight compounds. Depolymerization agents can also include methods and conditions that provide one or more of low molecular weight aldehydes, alcohols, or carboxylic acids. In some cases, depolymerization agents can include methods and conditions that provide one or more of low molecular weight aromatic aldehydes, alcohols, or carboxylic acids. In other cases, depolymerization agents can include methods and conditions that provide a high yield (e.g., 5%, 10%, 15%, 20%, 25%, 30%, 35%, 40%, 45%, 50%, 55%, 60%, 65%, 70%, 75%, 80%, 85%, 90%, 95%, 99% or more) of aromatic aldehydes, alcohols, or carboxylic acids. In some embodiments, depolymerization agents can include methods and conditions that efficiently convert lignin, e.g. convert 35%, 40%, 50%, 55%, 60%, 65%, 70%, 75%, 80%, 85%, 90%, 95%, 99%, or 100% of the lignin in the starting material (e.g., lignin or lignocellulosic biomass) into low molecular weight compounds.

Depolymerization agents of the present invention can include methods and conditions that predominantly yield low molecular weight aldehydes or low molecular weight aromatic aldehydes. In some cases, depolymerization agents can include methods and conditions that provide, or generally provide, a high yield of aldehydes or aromatic aldehydes. Additionally, depolymerization agents can include methods and conditions that provide more aldehydes than carboxylic acids or more aldehydes than alcohols.

Depolymerization agents include the methods and conditions provided in Pearl, (1942). For example, lignin or lignocellulosic biomass may be contacted with $CuSO_4$ and NaOH under conditions that yield aldehydes. In some cases, depolymerization agents, such as $CuSO_4$ and NaOH can be utilized to yield particular aldehydes including vanillin and syringaldehyde. Depolymerization agents also include the methods and conditions provided in Liu, (2013). For example, lignin or lignocellulosic biomass may be contacted with quaternary ammonium and imidazolium dimethylphosphate ionic liquids. Such conditions are known to efficiently depolymerize lignin and provide aldehydes such as vanillin, p-hydroxybenzaldehyde, and syringaldehyde in moderate yields.

Depolymerization agents of the present invention can include methods and conditions provided in Villar, (*Wood*

*Science and Technology* 35 (3), 245-255, 2001). For example, lignin or lignocellulosic biomass may be contacted with mild oxidants such as nitrobenzene, metal oxides, and oxygen to produce aldehydes. Similarly, depolymerization with metal organic frameworks of $Cu^{2+}$, $Fe^{3+}$, or combinations of metal ions can be used as oxidants for lignin depolymerization. Alternatively, hydrogen peroxide or Fenton's reagent may be utilized for oxidative lignin depolymerization. As yet another embodiment, oxidation may be performed under alkaline conditions.

Depolymerization agents of the present invention can include methods and conditions that predominantly yield low molecular weight alcohols or low molecular weight aromatic alcohols. In some cases, depolymerization agents can include methods and conditions that provide, or generally provide, a high yield of alcohols or aromatic alcohols. Additionally, depolymerization agents can include methods and conditions that provide more alcohols than carboxylic acids or more alcohols than aldehydes. In some cases, depolymerization can include methods that provide phenols, a high yield of phenols, phenols as a predominant product, or a greater proportion of phenols as compared to carboxylic acids or aldehydes.

Depolymerization agents include the methods and conditions provided in Kleen, (1991). For example lignocellulosic biomass may be subject to fast pyrolysis. In some cases, fast pyrolysis depolymerization can provide alcohols such as 4-Methyl guaiacol, 4-vinyl guaiacol, trans-isoeugenol, trans-coniferyl alcohol, and aldehydes such as vanillin, and coniferaldehyde as the predominant products of lignin depolymerization. In some cases, fast pyrolysis can result in alcohols such as guaiacol, 4-vinyl guaiacol, and trans-isoeugenol as the predominant products of lignin depolymerization. In still other cases, pyrolysis can provide guaiacol, syringol, and 4-vinyl syringol as the predominant products of lignin depolymerization.

Depolymerization agents include the methods and conditions for hydrogenolysis. In some cases, hydrogenolysis can provide phenols. In some cases, hydrogenolysis is performed at about 300-600° C. in the presence of an active hydrogen donator such as a solvent or hydrogen gas. Suitable hydrogen donating solvents include tetralin, sodium formate, or formic acid.

Depolymerization conditions also include base catalyzed depolymerization, such as described in U.S. Pat. No. 5,959,167. For example, the lignin can be contacted with a base (e.g., an alkali hydroxide) in the presence of a supercritical alcohol (e.g., methanol, ethanol, etc.). In some cases, the base catalyzed depolymerization can provide a mixture of depolymerized lignin products including alkylated phenols (e.g., mono, di, tri, and polysubstituted phenols and alkylated benzenes), alkylated benzenes, and alkoxybenzenes.

Depolymerization can be performed at any suitable temperature, pressure, or pH. Suitable temperatures, pressures, and pH for depolymerization can be determined by those of skill in the art. In some cases, the ionic liquids of the present invention provide for pre-treatment or lignin depolymerization at a reduced temperature or pressure.

Lignin may be depolymerized and the depolymerization products can be purified. Methods and compositions are known in the art for purifying lignin depolymerization products. In some cases, a purification method may be chosen that yields one or more of lignin derived alcohols, aldehydes, or carboxylic acids.

In some embodiments, the method comprises a further step of contacting a starting material with a depolymerization agent includes contacting the starting material with one or more of the following compositions: an ionic liquid such as an imidazolium ionic liquid or a lignin-derived ionic liquid; a hydrogen gas; a hydrogen gas and a catalyst; a hydrogen donating solvent such as tetralin, sodium formate, and formic acid; a dilute acid; a concentrated acid; a base; a catalyst and an oxidizing agent such as nitrobenzene, metal oxide, hydrogen peroxide, or oxygen gas; Fenton's reagent; a metal organic framework of copper or iron; or ammonium hydroxide. In some embodiments, the depolymerization agent is a lignin derived ionic liquid. In some embodiments, the depolymerization agent is an imidazolium ionic liquid. The starting material comprises lignin. The starting material can be a hardwood, softwood, or grass, or lignin waste from a biorefiner, or a pulp or paper manufacturer. "Depolymerization agent" refers to any chemical or process for depolymerizing lignin. Exemplary depolymerization agents include $CuSO_4$/NaOH (Pearl, 1942), and the chemicals and processes provided in Pandey, 2011. Depolymerization agents can include ionic liquids, including alkyl-imidazolium ionic liquids, and lignin derived ionic liquids.

Aldehyde lignin depolymerization products include:

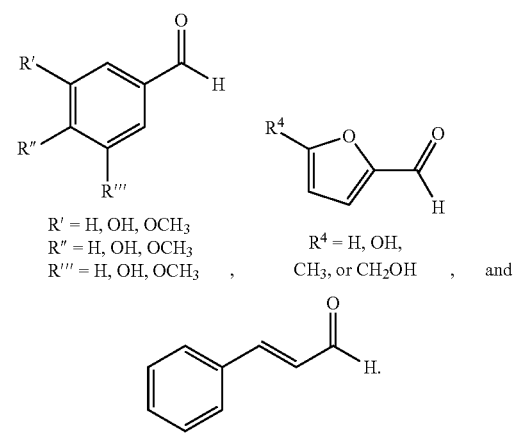

$R' = H, OH, OCH_3$
$R'' = H, OH, OCH_3$
$R''' = H, OH, OCH_3$ , $R^4 = H, OH,$
$CH_3$, or $CH_2OH$ , and Alcohol lignin depolymerization products include p-coumaryl alcohol, coniferyl alcohol, sinapyl alcohol,

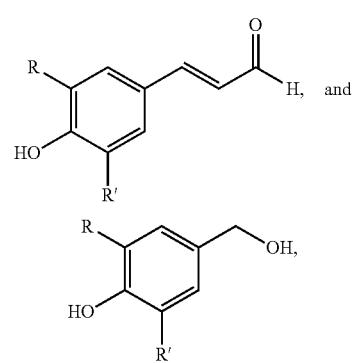

wherein R and R' are selected from the group consisting of H and $OCH_3$.

Alcohol lignin depolymerization products also include the following phenols:

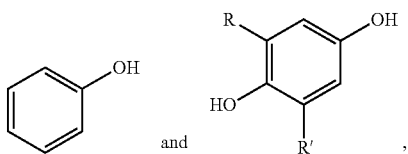

wherein R and R' is independently selected from the group consisting of H and OCH$_3$.

Lignoacid depolymerization products of the present invention include the following carboxylic acids:

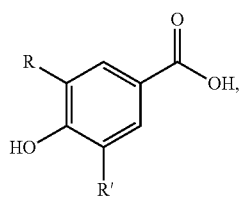

where R and R' are each selected from the group consisting of H, CH$_3$, OH, and OCH$_3$.

In some cases lignin depolymerization products, e.g., vanillin, syringaldehyde, a lignin derived aldehyde, or a derivative thereof, can be converted to a methoxy, dimethoxy or trimethoxy derivative. For example, vanillin can be converted into 3,4dimethoxybenzaldehyde. As another example, syringaldehyde can be converted into 3,4,5 trimethoxybenzaldehyde. The conversion can be performed using methods known in the art. For example, vanillin, syringaldehyde, and/or another lignin derived aldehyde can be dissolved in aqueous alkaline hydroxide (e.g., NaOH), to which an alkylating agent such as dimethylsulfate is added under reflux conditions for at least about 30 minutes-1 h or more. In some cases, the desired methoxy derivative is obtained as a phase separated oil.

REFERENCES CITED

1. J. H. Clark et al., Green chemistry and the biorefinery: a partnership for a sustainable future. *Green Chemistry* 8, 853 (2006).
2. M. E. Himmel et al., Biomass recalcitrance: Engineering plants and enzymes for biofuels production. *Science* 315, 804-807 (2007).
3. A. J. Ragauskas et al., Lignin valorization: improving lignin processing in the biorefinery. *Science* 344, 1246843 (2014).
4. J. Zaldivar, J. Nielsen, L. Olsson, Fuel ethanol production from lignocellulose: a challenge for metabolic engineering and process integration. *Applied Microbiology and Biotechnology* 56, 17-34 (2001).
5. M. G. Wiebe, K. Koivuranta, M. Penttila, L. Ruohonen, Lipid production in batch and fed-batch cultures of *Rhodosporidium toruloides* from 5 and 6 carbon carbohydrates. *Bmc Biotechnology* 12, (2012).
6. Z. W. Zhu et al., A multi-omic map of the lipid-producing yeast *Rhodosporidium toruloides*. *Nature Communications* 3, (2012).
7. J. M. Ageitos, J. A. Vallejo, P. Veiga-Crespo, T. G. Villa, Oily yeasts as oleaginous cell factories. *Applied Microbiology and Biotechnology* 90, 1219-1227 (2011).
8. S. Zhang et al., Engineering *Rhodosporidium toruloides* for increased lipid production. *Biotechnol Bioeng* 113, 1056-1066 (2016).
9. X. P. Lin et al., Functional integration of multiple genes into the genome of the oleaginous yeast *Rhodosporidium toruloides*. *Ferns Yeast Research* 14, 547-555 (2014).
10. Y. B. Liu et al., Characterization of glyceraldehyde-3-phosphate dehydrogenase gene RtGPD1 and development of genetic transformation method by dominant selection in oleaginous yeast *Rhodosporidium toruloides*. *Applied Microbiology and Biotechnology* 97, 719-729 (2013).
11. C. M. J. Koh, Y. B. Liu, Moehninsi, M. G. Du, L. H. Ji, Molecular characterization of KU70 and KU80 homologues and exploitation of a KU70-deficient mutant for improving gene deletion frequency in *Rhodosporidium toruloides*. *Bmc Microbiology* 14, (2014).
12. F. Xu et al., Transforming biomass conversion with ionic liquids: process intensification and the development of a high-gravity, one-pot process for the production of cellulosic ethanol. *Energy & Environmental Science* 9, 1042-1049 (2016).
13. J. Sun et al., CO2 enabled process integration for the production of cellulosic ethanol using bionic liquids. *Energy & Environmental Science*, 2822-2834 (2016).
14. T. J. Maimone, P. S. Baran, Modern synthetic efforts toward biologically active terpenes. *Nature Chemical Biology* 3, 396-407 (2007).
15. D. K. Ro et al., Production of the antimalarial drug precursor artemisinic acid in engineered yeast. *Nature* 440, 940-943 (2006).
16. P. P. Peralta-Yahya et al., Identification and microbial production of a terpene-based advanced biofuel. *Nature Communications* 2, (2011).
17. K. E. J. Tyo, P. K. Ajikumar, G. Stephanopoulos, Stabilized gene duplication enables long-term selection-free heterologous pathway expression. *Nature Biotechnology* 27, 760-U115 (2009).
18. J. Yin et al., Effects of chromosomal gene copy number and locations on polyhydroxyalkanoate synthesis by *Escherichia coli* and *Halomonas* sp. *Applied Microbiology and Biotechnology* 99, 5523-5534 (2015).
19. E. M. Paradise, J. Kirby, R. Chan, J. D. Keasling, Redirection of flux through the FPP branch-point in *Saccharomyces cerevisiae* by down-regulating squalene synthase. *Biotechnol Bioeng* 100, 371-378 (2008).
20. J. Kirby et al., Use of Nonionic Surfactants for Improvement of Terpene Production in *Saccharomyces cerevisiae*. *Applied and Environmental Microbiology* 80, 6685-6693 (2014).
21. A. R. Apel, M. Ouellet, H. Szmidt-Middleton, J. D. Keasling, A. Mukhopadhyay, Evolved hexose transporter enhances xylose uptake and glucose/xylose co-utilization in *Saccharomyces cerevisiae*. *Scientific Reports* 6, (2016).
22. D. Groff et al., Supplementation of Intracellular XylR Leads to Coutilization of Hemicellulose Sugars. *Applied and Environmental Microbiology* 78, 2221-2229 (2012).
23. C. L. Li, L. Sun, B. A. Simmons, S. Singh, Comparing the Recalcitrance of Eucalyptus, Pine, and Switchgrass Using Ionic Liquid and Dilute Acid Pretreatments. *Bioenergy Research* 6, 14-23 (2013).
24. J. Shi et al., Impact of Pretreatment Technologies on Saccharification and Isopentenol Fermentation of Mixed Lignocellulosic Feedstocks. *Bioenergy Research* 8, 1004-1013 (2015).
25. S. Singh et al., Comparison of different biomass pretreatment techniques and their impact on chemistry and structure. *Front. Energy Res.* 2, (2015).

26. M. J. Liszka et al., Switchable ionic liquids based on di-carboxylic acids for one-pot conversion of biomass to an advanced biofuel. *Green Chem.* 18, 4012-4021 (2016).
27. S. Fillet et al., Fatty alcohols production by oleaginous yeast. *Journal of Industrial Microbiology & Biotechnology* 42, 1463-1472 (2015).
28. P. Buzzini et al., Carotenoid profiles of yeasts belonging to the genera *Rhodotorula, Rhodosporidium, Sporobolomyces*, and *Sporidiobolus. Canadian Journal of Microbiology* 53, 1024-1031 (2007).
29. T. S. Ham et al., Design, implementation and practice of JBEI-ICE: an open source biological part registry platform and tools. *Nucleic Acids Research* 40, (2012).
30. E. P. Abbott, G. Ianiri, R. Castoria, A. Idnurm, Overcoming recalcitrant transformation and gene manipulation in Pucciniomycotina yeasts. *Applied Microbiology and Biotechnology* 97, 283-295 (2013).
31. B. Ozaydin, H. Burd, T. S. Lee, J. D. Keasling, Carotenoid-based phenotypic screen of the yeast deletion collection reveals new genes with roles in isoprenoid production. *Metab Eng* 15, 174-183 (2013).
32. I. R. Sitepu et al., Oleaginous yeasts for biodiesel: current and future trends in biology and production. *Biotechnol Adv* 32, 1336-1360 (2014).
33. J. J. Lee, L. Chen, J. Shi, A. Trzcinski, W. N. Chen, Metabolomic profiling of *Rhodosporidium toruloides* grown on glycerol for carotenoid production during different growth phases. *J Agric Food Chem* 62, 10203-10209 (2014).
34. B. J. Park S, Himmel M E, Parilla P A, Johnson D K, Research cellulose crystallinity index: measurement techniques and their impact on interpreting cellulase performance. *Biotechnol Biofuels* 3, (2010).
35. L. M. Mansikkamäki P, Rissanen K, Structural changes of cellulose crystallites induced by mercerisation in different solvent systems; determined by powder X-ray diffraction method. *Cellulose* 12, 233-242 (2005).

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Red Yeast for Conversion of Depolymerized Cellulose, Hemicellulose, and Lignin into Bioproducts Economical conversion of lignocellulosic biomass to biofuels and bioproducts is central to the establishment of a robust bioeconomy. Efficient conversion of lignocellulose requires the utilization of all its primary components (cellulose, hemicellulose, and lignin), yet no microbe in commercial use today can achieve this feat. To that end, *Rhodosporidium toruloides* was engineered to produce two non-native terpenes with biofuel (bisabolene) and pharmaceutical (amorphadiene) applications from a mixture of depolymerized cellulose (glucose), hemicellulose (xylose), and lignin (p-coumaric acid). It was cultivated on corn stover hydrolysates prepared by two different pretreatment methods, including one using the novel biocompatible ionic liquid choline α-ketoglutarate. This study establishes *R. toruloides* as a new platform for the simultaneous conversion of depolymerized cellulose, hemicellulose, and lignin into biofuels and bioproducts.

While well-established microbes such as *Escherichia coli* and *Saccharomyces cerevisiae* are convenient hosts for bioproduct synthesis from glucose or xylose, they do not readily utilize multiple carbon sources simultaneously, especially not those derived from lignin, making it difficult to efficiently use hydrolyzed lignocellulose as a carbon source (4). Two approaches to circumvent this problem are to 1) engineer commonly used hosts such as *E. coli* and *S. cerevisiae* to efficiently utilize cellulose, hemicellulose, and lignin depolymerization products, or 2) find a host that naturally has this ability and engineer it to make bioproducts. *Rhodosporidium toruloides*, an oleaginous, carotenogenic basidiomycete yeast, has been studied as a model organism for lipid production and has been shown to co-utilize both hexose and pentose sugars (5), suggesting potential advantages of *R. toruloides* over conventional lignocellulosic conversion hosts. *R. toruloides* accumulates high concentrations of lipids and carotenoids, both of which are derived from acetyl-CoA (6). This suggests that it may be a promising host for the production of compounds synthesized from acetyl-CoA, especially terpene and lipid-based bioproducts. Not only does it make these natural bioproducts, it can also grow to very high cell densities (100 g/L dry cell mass) (7), another important industrially-relevant characteristic.

Taking advantage of the recently developed genetic tools for *R. toruloides* (8-11), we explored its utility as a new platform for non-native terpene production from lignocellulose. We demonstrate that *R. toruloides* has the unique ability to simultaneously utilize glucose and xylose derived from cellulose and hemicellulose in addition to lignin depolymerization products, such as p-coumaric acid, opening the possibility of complete lignocellulose conversion, a process that would increase the efficiency and commercial viability of a biorefinery. Finally, we demonstrate that *R. toruloides* is compatible with a single-unit or one-pot lignocellulose pretreatment, saccharification, and fermentation process (FIG. 1B, Panel a) that reduces biorefinery capital and operating expenses (CAPEX, and OPEX, respectively) and wastewater treatment (12, 13). Together, these abilities suggest that *R. toruloides* is a very promising host for the conversion of the majority of the carbon present in lignocellulose into advanced biofuels and bioproducts.

Figure 1B:
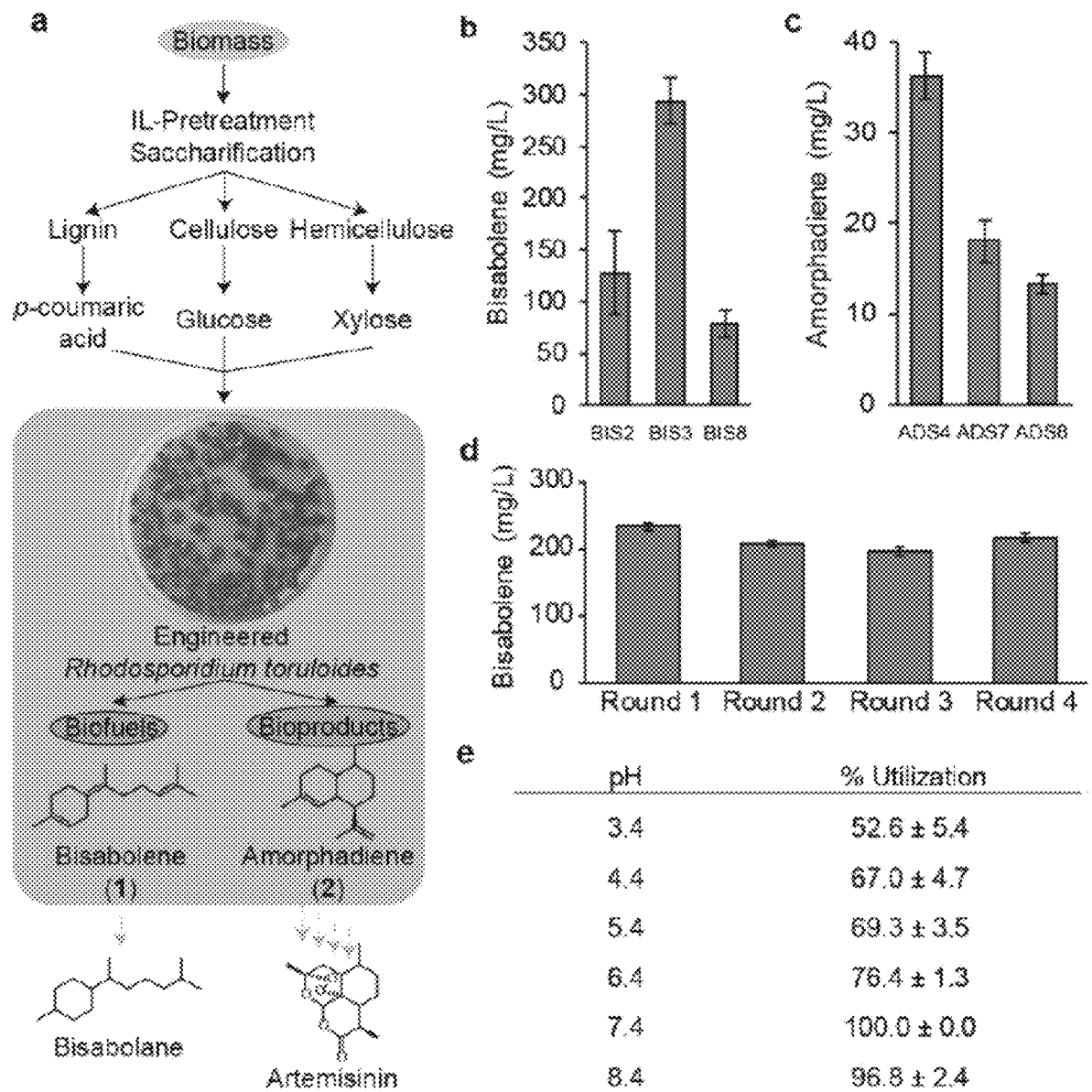
FIG. 1B. Overview and characterization of R. toruloides as a new platform for production of lignocellulosic biofuels and bioproducts. (Panel a) Schematic of lignocellulose conversion process. (Panel b) Bisabolene and (Panel c) amorphadiene titers in selected strains grown in SD+2% glucose. 5 mL cultures in test tubes were set up at a starting OD of 0.1 with a 20% dodecane overlay. At day 7, the dodecane layer was sampled and analyzed for bisabolene measurement. (n=3, data shown as average±s.d, representative from two individual experiments). (Panel d) Stability of bisabolene production in cultures passaged every 6 days (n=3, data shown as average±s.d, from a single experiment). (Panel e) Percent utilization of glucose in SD media starting at various pH. Cultures were carried out as described above, the aqueous layer was sampled for glucose analysis (n=3, data shown as average±s.d, from a single experiment).

Terpenes are produced by a variety of organisms and have a wide range of applications from flavors, fragrances, and pharmaceuticals to biofuels and chemical feedstocks (14). In this study, we selected two terpenes, amorphadiene and bisabolene, to examine the suitability of *R. toruloides* as a conversion host. Amorphadiene, a precursor of the antimalarial drug artemisinin, was chosen as an example of a commercially relevant bioproduct (15) and bisabolene, an immediate precursor of the D2 diesel alternative bisabolane, was chosen as an example of an advanced "drop-in" biofuel (16). Codon optimized expression cassettes for bisabolene (BIS) and amorphadiene (ADS) synthases were constructed and separately integrated into the genome of *R. toruloides* IFO0880 using *Agrobacterium tumefaciens* mediated transformation (ATMT) (8). A number of transformants were confirmed to produce either bisabolene (FIG. 1B, Panel b) or amorphadiene (FIG. 1B, Panel c), with variance in titer between strains most likely due to copy number and integration site effects (17, 18). Terpene titers for selected strains in synthetic defined (SD) medium containing 2% (w/v) glucose, reached 294 mg/L for bisabolene and 36 mg/L for amorphadiene. These bisabolene and amorphadiene titers attained in R. toruloides are highly encouraging considering that they exploit the natural flux of carbon through this yeast's native terpene biosynthetic pathway. In comparison, the yeast S. cerevisiae transformed with high copy plasmids harboring the BIS and ADS genes and grown in equivalent media attained significantly lower bisabolene and amorphadiene titers—approximately 20 and 10 mg/L, respectively ((19) for ADS, unpublished data for BIS). Another notable feature of the R. toruloides BIS strain is that bisabolene titers show remarkable stability over extended periods of repeated cultivation, varying by less than 16% over the course of four cultures spanning 24 days (FIG. 1B, Panel d). It should be noted that this reproducibility was also achieved without the need for a heterologous inducer or antibiotic selection, since the BIS gene is stably integrated into the genome and expression is under control of a constitutive GAPDH promoter (8-10). Both of these features reduce OPEX in a biorefinery. In comparison, the bisabolene titer from an engineered strain of S. cerevisiae grown under similar conditions was found to decline by more than 75% over 14 days (20). The strain stability we observed in engineered R. toruloides is an important industrial phenotype and a critical factor for large-scale economical production of any bioproduct.

Figure 4:
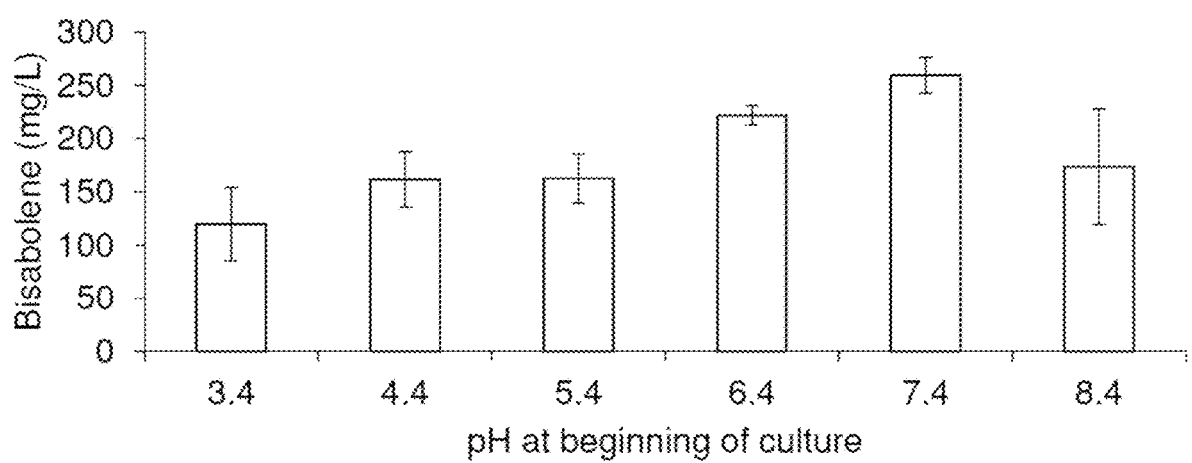
FIG. 4. Bisabolene titers of triplicate SD cultures starting at various pH. 5 mL cultures in test tubes were set up at a starting OD of 0.1 with a 20% dodecane overlay. At day 7, the dodecane layer was sampled and analyzed for bisabolene measurement. (n=3, data shown as average±s.d, from a single experiment).

We found that the pH of the growth medium is an important factor for efficient sugar utilization by R. toruloides. After examining a range of starting pH values in unbuffered medium (3 to 8) in batch cultures, a starting pH of 7.4 was determined to be optimal to achieve complete glucose utilization (FIG. 1B, Panel e) and the highest bisabolene titer (FIG. 4). Interestingly, R. toruloides grew and produced bisabolene at a pH as low as 3.4, suggesting the host may be amenable to production of organic acids or other bioproducts that require low pH. One potential explanation for the rapid decline in pH is that R. toruloides is producing native organic acids of potential value, a topic that merits further investigation. However, once the pH declines to 2.5 (in unbuffered medium starting at pH 7 or below), sugar utilization is strongly inhibited, suggesting that the pH must remain above this level to enable efficient carbon conversion. Therefore, all subsequent experiments in unbuffered media were performed with a starting pH of 7.4.

Figure 2:
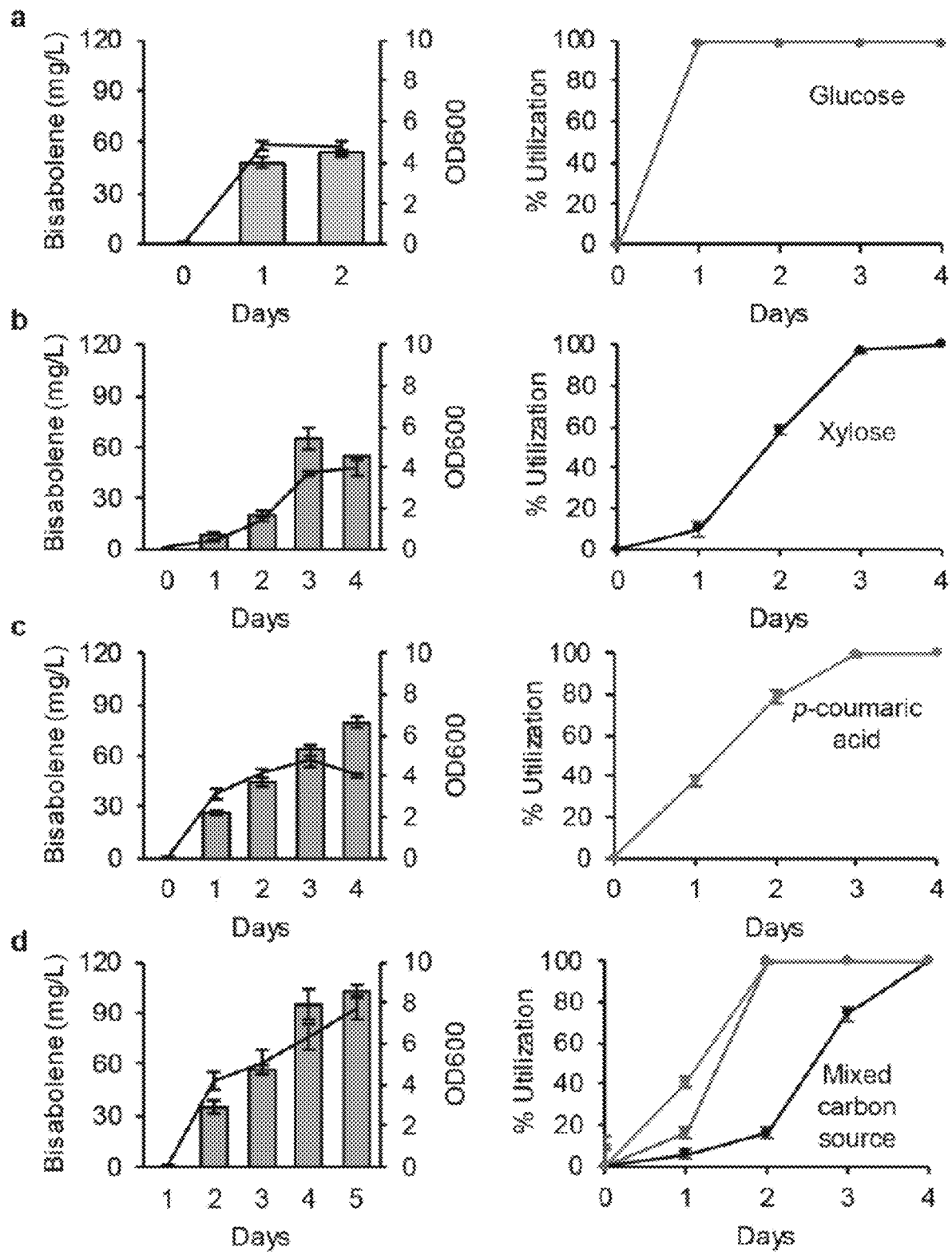
FIG. 2. R. toruloides is able to convert glucose, xylose, and p-coumaric acid, both individually and mixed, into bisabolene. Bisabolene titers, growth, and carbon utilization of strain BIS3 grown in SD supplemented with different carbon sources: (Panel a) 0.5% Glucose, (Panel b) 0.5% xylose, (Panel c) 0.5% p-coumaric acid, and (Panel d) 0.5% glucose, 0.5% xylose, 0.5% p-coumaric acid. Left panels: Lines represent ODs, bars represent bisabolene titers. Right panels: glucose (red), xylose (black), p-coumaric acid (blue). 5 mL cultures in test tubes were set up at a starting OD of 0.1 with a 20% dodecane overlay. At each time point, the dodecane layer was sampled and analyzed for bisabolene measurement and the aqueous layer was sampled for OD measurement and carbon source analysis (n=3, data shown as average±s.d, representative from at least four individual experiments).

To demonstrate the capability of engineered R. toruloides to utilize different carbon sources for the production of non-native terpenes, we cultivated the bisabolene-producing strain BIS3 with the most abundant sugars present in lignocellulosic hydrolysates: glucose and xylose, as well as a common lignin-degradation product found in hydrolysates (e.g. the hydrolysate in FIG. 3, Panels a to d), p-coumaric acid. Initially, these carbon sources were provided individually and growth, carbon utilization, and bisabolene production were monitored (FIG. 2, Panels a to c). Glucose was completely consumed at the fastest rate, followed by p-coumaric acid, then xylose (in 1, 3, and 4 days, respectively). The highest bisabolene titers were observed in the p-coumaric acid cultures, likely due to its higher percentage of carbon relative to the sugars (FIG. 2, Panels a to c). Remarkably, when combined, all three carbon sources were completely utilized within four days (FIG. 2, Panel d). The p-coumaric acid was actually completely utilized earlier in the presence of the other sugars (2 vs 3 days), while complete utilization of glucose and xylose took slightly longer when present in the mixture (glucose: 2 vs 1 day; xylose: both day 4 but less consumed by day 2 in the mixture).

Much effort has been expended on metabolic engineering of common microbial host organisms such as E. coli and S. cerevisiae for simultaneous utilization of multiple carbon sources, such as glucose and xylose (21, 22). The ability of R. toruloides to efficiently utilize multiple carbon sources, particularly hexose and pentose sugars combined with aromatic compounds, is something that even extensively engineered strains of S. cerevisiae and E. coli have been unable to accomplish. However, the decrease in glucose and xylose consumption rates in R. toruloides cultures grown on mixed sugars merits further investigation to determine if there is competitive sugar transport, catabolite repression or other mechanisms affecting the kinetics.

The performance of R. toruloides grown on purified substrates indicates that it may be an excellent biocatalyst for the conversion of deconstructed lignocellulose into valuable bioproducts. To test this premise, we examined how R. toruloides performs on substrates derived from actual lignocellulosic biomass. There are a number of technologies that have been developed to efficiently depolymerize biomass into intermediates suitable for microbial conversion, and those based on ionic liquid (IL) pretreatment and enzymatic saccharification have been demonstrated to be some of the most efficient and effective (23-25). Recently, biocompatible ILs that do not inhibit commercial cellulase enzyme mixtures or microbial growth have been developed, enabling single-unit operation biomass pretreatment, saccharification, and fermentation, potentially reducing both CAPEX and OPEX in a biorefinery (13, 26). Therefore, to test the performance of R. toruloides on a biomass hydrolysate, a corn stover hydrolysate containing glucose, xylose, and p-coumaric acid was generated using pretreatment with a novel biocompatible IL, choline $\alpha$-ketoglutarate ([Ch][$\alpha$-Kg]), followed by enzymatic saccharification. This IL falls into a recently developed class of ILs based on dicarboxylic acids (26). Compositional and X-ray diffraction data, suggest that the IL pretreatment reduced recalcitrance to enzymatic saccharification by removing high amounts of lignin from the biomass and reducing the cellulose crystallinity (Table 1 and FIG. 5).

Figure 3:
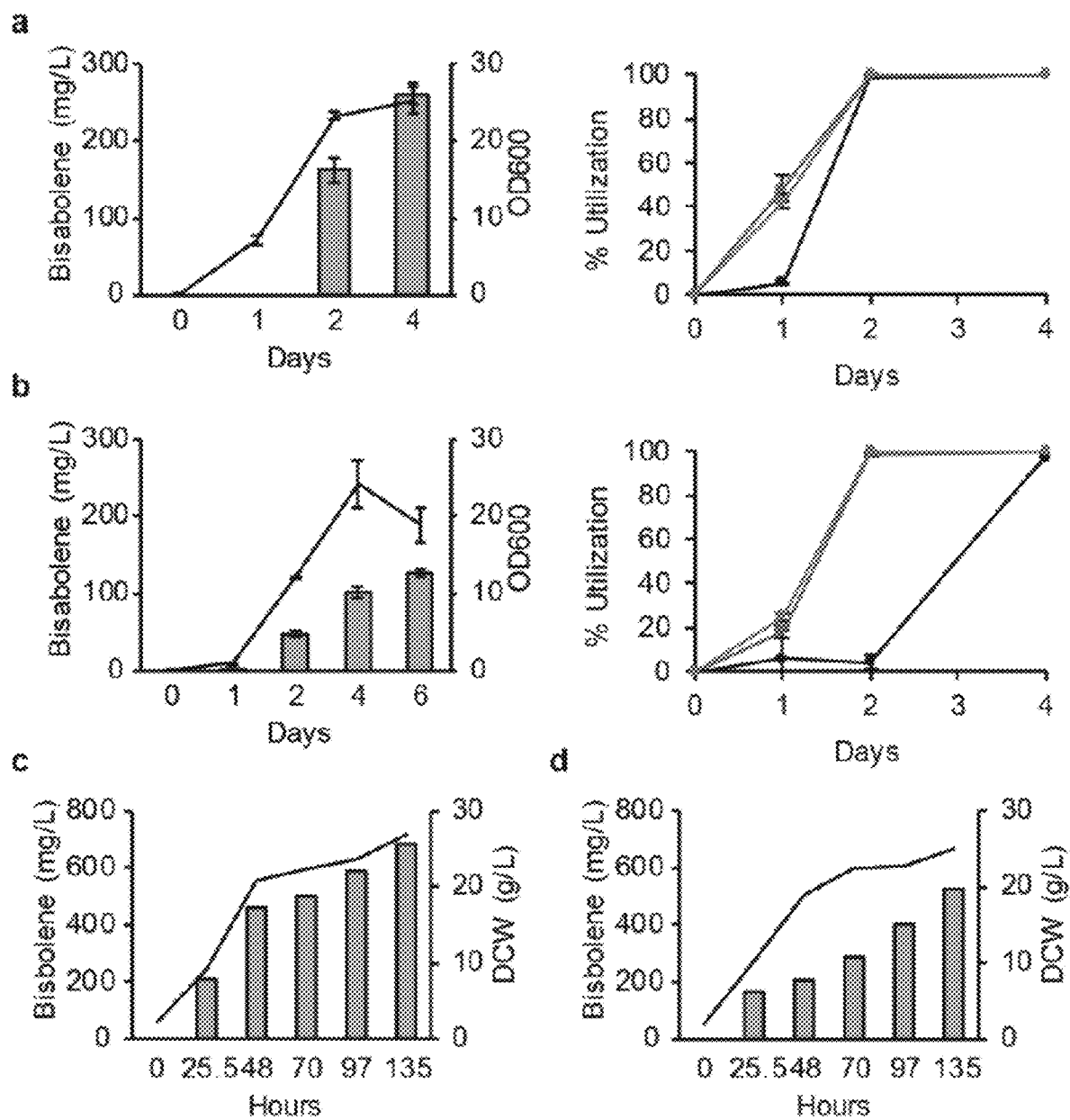
FIG. 3. *R. toruloides* is able to completely convert biomass-derived glucose, xylose, and p-coumaric acid into bisabolene and is amenable to high-carbon fed-batch fermentation. Bisabolene titers, growth, and carbon source utilization of strain BIS3 grown in (Panel a) corn stover hydrolysate and (Panel b) SD supplemented with individual components at the same concentration as those found in the corn stover hydrolysate: glucose (17.1 g/L), xylose (9.1 g/L), p-coumaric acid (383 mg/L), alpha-ketoglutarate (254 mM), and choline (586 mM). A low level of arabinose (0.98 g/L) was also detected in the hydrolysate and included in the control medium. Left panels: Lines represent ODs, bars represent bisabolene titers. Right panels: glucose (red), xylose (black), p-coumaric acid (blue). 5 mL cultures in test tubes were set up at a starting OD of 0.1 with a 20% dodecane overlay. At each time point, the dodecane layer was sampled and analyzed for bisabolene measurement and the aqueous layer was sampled for OD measurement and carbon source analysis (n=3, data shown as average±s.d, representative from at least two individual experiments). Bioreactor cultivation of strain BIS3 in (Panel c) alkaline hydrolysate (Panel d) SD+glucose. Lines represent dry cell weight (DCW), bars represent bisabolene titers. Bisabolene titers were measured three times per time point, average value is shown. At each time point, 10 mL of the culture was sampled. After separation, the dodecane layer was used for bisabolene measurement. 5 mL of the aqueous layer was used for the measurement of DCW.

R. toruloides was able to grow in the [Ch][$\alpha$-Kg] hydrolysate, consuming glucose, xylose, and p-coumaric acid, and producing 261±14 mg/L of bisabolene (FIG. 3, Panel a). In fact, it produced higher titers of bisabolene in the hydrolysate than it did in a control medium with matching concentrations of the IL, sugars, and p-coumaric acid (127±5 mg/L) (FIG. 3, Panel b). In addition to p-coumaric acid (H unit of lignin), analysis of the hydrolysate also identified much very low levels of other lignin-depolymerization products, such as ferulic acid and sinapic acid, from the G and S units of lignin, respectively. The other aromatic compounds also appear to be utilized (data not shown), indicating that R. toruloides will be able to consume a good fraction of lignin as biomass deconstruction technologies advance to provide more extensive lignin depolymerization.

Figure 6:
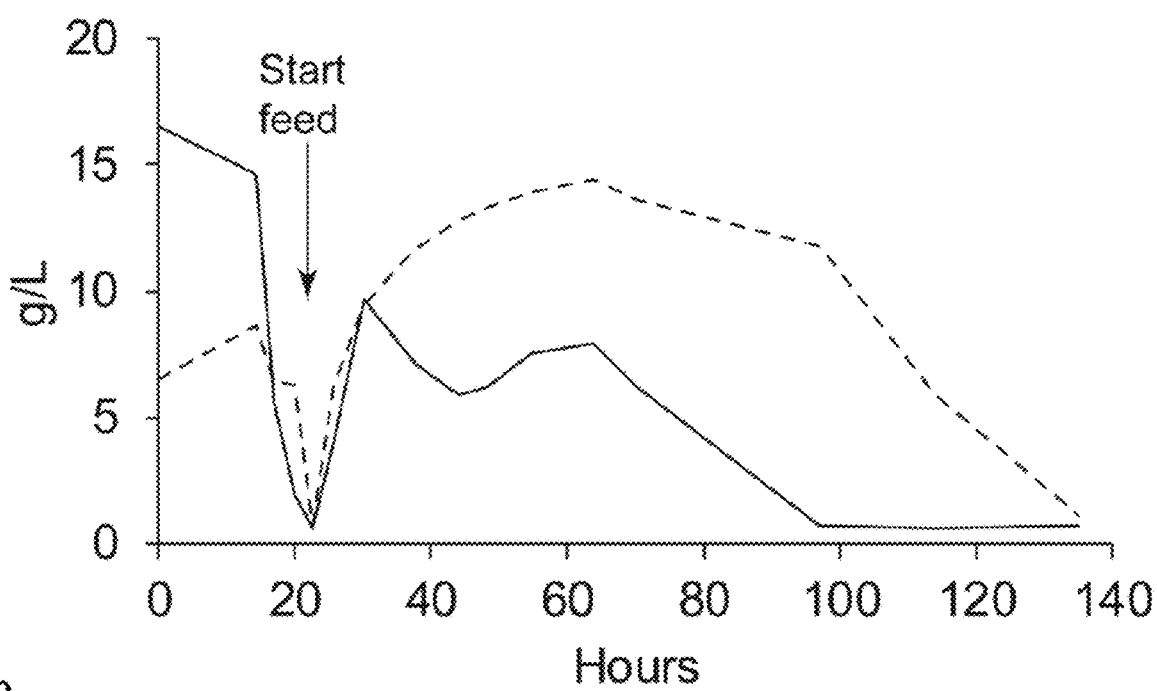
FIG. 6. Measured carbon source concentration profiles from bioreactor fermentations in (Panel a) alkaline hydrolysate and (Panel b) SD+ glucose. Solid lines represent glucose, dashed lines represent xylose.
Figure 6:
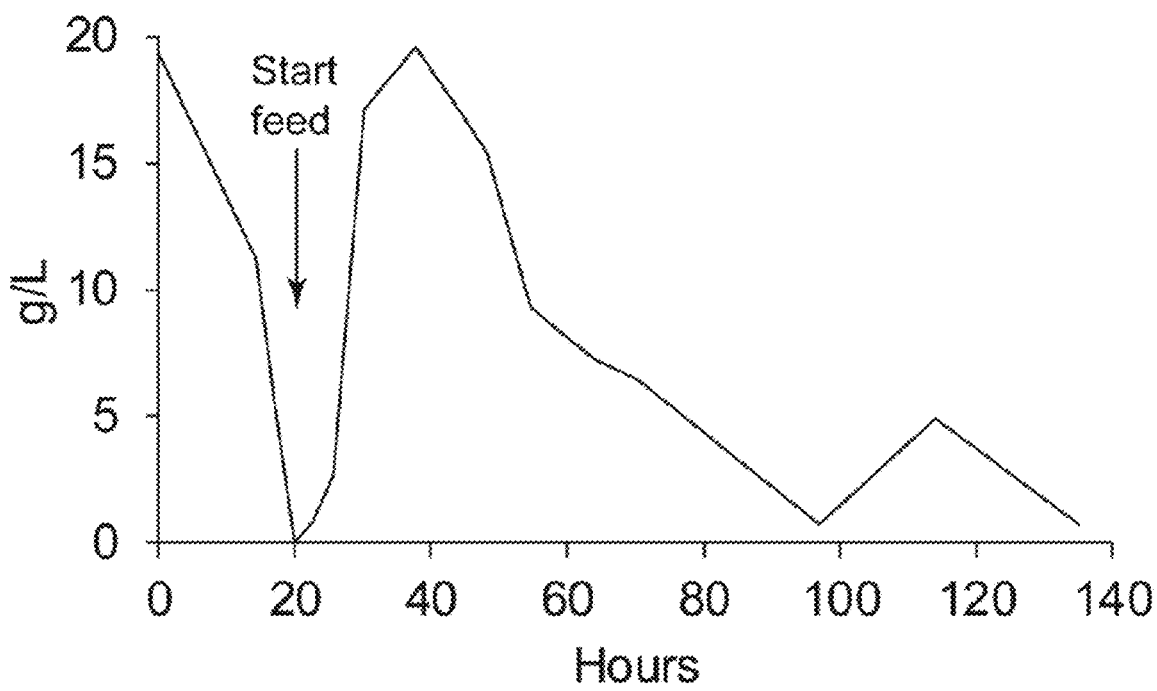

In order to examine the spectrum of hydrolysates that R. toruloides can utilize and determine the impact of optimized cultivation conditions on bisabolene titers, a corn stover hydrolysate generated from an alkaline pretreatment was also tested. This pretreatment method generates very high concentrations of glucose and xylose, so it can be used for high-gravity fed-batch cultivation, which enables the addition of much more carbon than the batch cultivations conducted with the [Ch][$\alpha$-Kg] hydrolysate. The drawback to this approach is that lignin depolymerization products are removed during the process, so only glucose and xylose utilization can be examined. *R. toruloides* was cultivated in a controlled, high-gravity fed-batch bioreactor using the alkaline corn stover hydrolysate or a glucose-only control medium, and produced 680 mg/L and 521 mg/L bisabolene, respectively (FIG. 3, Panels c, d). The lower titer in the control may be due to the lower amount of sugars added to the cultivation (alkaline: 73.8 g/L and control: 61.5 g/L, FIG. 6, Panels a, b), resulting in a slightly lower dry cell weight (alkaline: 27 g/L and control: 25 g/L) and lower bisabolene production. It is interesting to note that *R. toruloides* produced higher titers of bisabolene in both hydrolysates versus their control media. In many instances, the opposite has been observed for organisms like *S. cerevisiae* and *E. coli*, further demonstrating the greater suitability of *R. toruloides* as a lignocellulosic conversion host.

Figure 7:
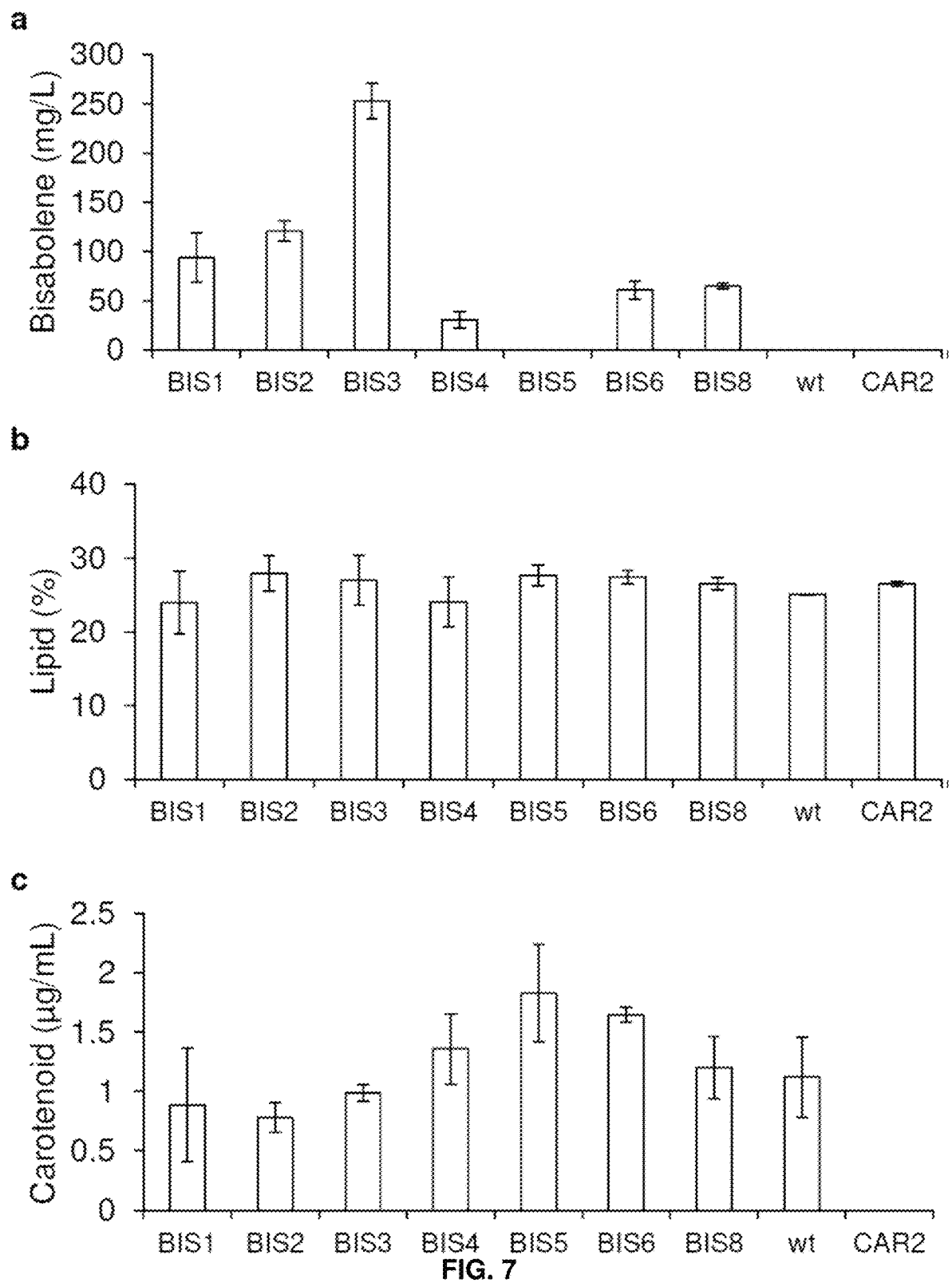
FIG. 7. Comparison of (Panel a) bisabolene titers, (Panel b) lipid content, and (Panel c) carotenoid levels between different triplicate cultures of BIS transformants. (n=3, data shown as average±s.d, from a single experiment).

These results show that *R. toruloides* is amenable to high-carbon fed-batch fermentations, which is another important feature when considering organisms for use in industry. The titer of 680 mg/L is impressive relative to those produced by strains of *S. cerevisiae* and *E. coli* that have undergone extensive genetic engineering (15, 16, 19). In addition, no significant reduction in the native pools of lipids or carotenoids was observed in the bisabolene-producing strains compared to wild type, suggesting that significant increases in titer can be achieved by further strain engineering to divert carbon flux away from these native molecules (both of which are derived from acetyl-CoA) toward bisabolene (FIG. 7, Panels a to c).

*Rhodosporidium toruloides* is emerging as a promising new production platform for the conversion of lignocellulose into biofuels and bioproducts. Much effort has focused on its oleaginous properties (high lipid proportions; >60% w/w of cell mass), and it has been engineered to produce several lipid derivatives (8, 27). It has also been examined for its production of potentially valuable native carotenoids: β-carotene, torularhodin and toluene (28). In this study, we demonstrate that this organism is a versatile production host that possesses many features critical to reducing CAPEX and OPEX in a biorefinery: 1) it can be used to make a variety of bioproducts, including non-native terpenes with biofuel and pharmaceutical applications, 2) heterologous production of bioproducts does not require inducers or antibiotics and is stable through multiple generations, 3) it can efficiently utilize both the polysaccharide and lignin fractions of inexpensive, carbon neutral, and renewable lignocellulosic feedstocks, 4) it is compatible with single-unit operation pretreatment, saccharification and fermentation bioprocessing configurations, and 5) bioproduct productivity is not inhibited in lignocellulosic hydrolysates. No other microbial production platform has been demonstrated to harbor all these properties, and *R. toruloides* sets a new standard for biotechnological applications that support a green economy.

Methods:

Media

Synthetic defined (SD) media were made following manufacturers' instructions with Difco yeast nitrogen base without amino acids (Becton, Dickinson & Co., Sparks, Md.) and Complete Supplemental Mixture (CSM; Sunrise Science Products, San Diego, Calif.). Initial medium pH was adjusted to 7.4 with NaOH unless otherwise stated. Luria Broth (LB) and Yeast Peptone Dextrose (YPD) media were made using pre-mixed Difco LB broth and Difco YPD broth.

Growth Conditions

*R. toruloides* seed cultures were obtained by inoculating 5 mL LB with single colonies from a YPD agar plate containing antibiotics at the following concentrations: nourseothricin, 100 µg/mL, and cefotaxime, 300 µg/mL. The seed cultures were used to inoculate 5 mL SD media with a starting optical density at 600 nm ($OD_{600}$) of 0.1. Cultures of terpene-producing strains were overlaid with 20% (v/v) dodecane. All cultures were grown at 30° C. with shaking at 200 rpm. Growth was monitored by measuring $OD_{600}$. Samples in which the OD measurements were significantly different from others in the sample set were excluded from the analysis.

Plasmid Construction and Transformation

Strains and plasmids used in this study can be found in Table 2, and are also available through the Joint BioEnergy Institute Strain Registry (at the website for: public-registry.jbei.org/(29)) and are available upon request.

Codon optimization, gene synthesis, and plasmid construction were performed by GenScript (Piscataway, N.J.). The genes encoding bisabolene synthase (BIS) and amorphadiene synthase (ADS) were codon optimized for *R. toruloides* based on a custom IFO0880 codon usage table (at the website for: genome.jgi.doe.gov/Rhoto_IFO0880_2/Rhoto_IFO0880_2.home.html), and the constructs were designed so that each gene was positioned between the GAPDH promoter and NOS terminator (9). The constructs were synthesized and inserted into the ATMT plasmid pGI2 (30) using the EcoRV restriction sites.

Measurement of Bisabolene and Amorphadiene

For measurement of bisabolene production, 10 µL of the dodecane overlay was sampled and diluted into 390 µL of ethyl acetate spiked with 1 mg/L caryophyllene as an internal standard. Bisabolene was quantified by gas chromatography-mass spectrometry (GC-MS) as described previously (31).

Assessment of Genetic Stability of the Bisabolene-Producing Strain BIS3

Strain BIS3 was cultured overnight in LB and, after removal of medium, cells were used to inoculate 5 mL of SD medium containing 2% (w/v) glucose at a starting $OD_{600}$ of 0.1, in triplicate. Cultures were overlaid with 20% dodecane and incubated by shaking at 200 rpm at 30° C. After 6 days the cultures were used to inoculate fresh medium of the same type and dodecane was sampled to quantify bisabolene production. This process was repeated 2 additional times, spanning four rounds of culture over 24 days.

Measurement of Lipid and Carotenoid Content

Total lipid content was quantified gravimetrically following extraction with Folch reagent (2:1 chloroform/methanol) as described previously (32). Carotenoids were extracted with acetone and quantified by HPLC as described previously (33). Carotenoid standards β-carotene, toluene, and torularhodin were obtained from Carotenature, GmbH (Ostermundigen, Switzerland).

Analysis of Sugars and α-Ketoglutarate

The concentrations of sugars and α-ketoglutarate were quantified on an Agilent Technologies 1200 series HPLC equipped with an Aminex HPX-87H column (BioRad, Hercules, Calif.) as described previously (20). Sugars were monitored by refractive index detector, and α-ketoglutarate was monitored by diode array detector at 210 nm. Concentrations were calculated by integration of peak areas and comparison to standard curves for the compounds of interest.

Analysis of p-Coumaric Acid

The concentrations of p-coumaric acid were quantified on an Agilent Technologies 1200 series HPLC equipped with a Zorbax Eclipse XDB-C18 column (Agilent Technologies, Santa Clara, Calif.). Five microliters of each sample was injected onto the column and eluted isocratically with 20% (v/v) acetonitrile in $H_2O$ containing 0.5% acetic acid (v/v) at a flow rate of 1 mL/min for 10 minutes at a column temperature of 24° C. Detection of p-coumaric acid utilized a diode array detector at 310 nm and concentrations were calculated by comparison of peak areas to standard curves generated with high purity p-coumaric acid.

Preparation of the Ionic Liquid [Ch][α-Kg]

In a typical process, [Ch][OH] (46 wt % in $H_2O$) was mixed with α-ketoglutaric acid (40 wt % in $H_2O$) in a 2:1 weight ratio at room temperature. The pH of the resulting IL was measured by pH probe and was maintained at 13.5.

Ionic Liquid One-Pot Pretreatment and Saccharification

Cellulase (Cellic® CTec2; Batch #VCN10001, protein content 188 mg/mL) and hemicellulase (Cellic® HTec2; Batch #VHN00001, protein content 180 mg/ml) enzyme mixtures were received as gifts from Novozymes NA (Franklinton, N.C., USA), and mixed with the volume ratio of 9:1 before use. Corn stover was supplied by the Department of Chemical Engineering & Materials Science at Michigan State University. The biomass was ground by a Thomas-Wiley Mini Mill fitted with a 20-mesh screen (Model 3383-L10 Arthur H. Thomas Co., Philadelphia, Pa., USA) and analyzed for polysaccharide composition after drying (glucan 38.90%±0.04, xylan 24.77 wt %±0.01, and lignin 18.42 wt %±0.27).

In an integrated process, 40 g corn stover was mixed with 160 g [Ch][α-Kg] (40 wt % in $H_2O$) at a 20 wt % biomass loading in a 300 mL Parr reactor and pretreated at 120° C. for 4 h. After pretreatment, the slurry was diluted with DI-water to obtain a final IL concentration of 10 wt %. Before adding the enzyme mixture (CTec2/HTec2=9:1, v/v) for the saccharification, α-ketoglutaric acid (40 wt % in $H_2O$) was used to lower the pH of the system to 5. Enzymatic hydrolysis was conducted at 50° C. in a 1 L shake flask for 3 days with an enzyme loading of 20 mg protein/g corn stover. Titers were: glucose (17.1 g/L), xylose (9.1 g/L), and p-coumaric acid (383 mg/L).

The raw and pretreated corn stover were dried and characterized with powder X-ray diffraction (PXRD). The XRD analyses were performed on a PANalytical Empyrean X-ray diffractometer equipped with a PIXcel3D detector and operated at 45 kV and 40 kA using Cu Kα radiation (λ=1.5418 Å). The patterns were collected in the 2θ range from 5 to 60° with a step size of 0.039° and an exposure time of 300 seconds. A reflection-transmission spinner was used as a sample holder and the spinning rate was set at 8 rpm throughout the experiment. Crystallinity index (CrI) was determined by Segal's method (34).

Figure 5:
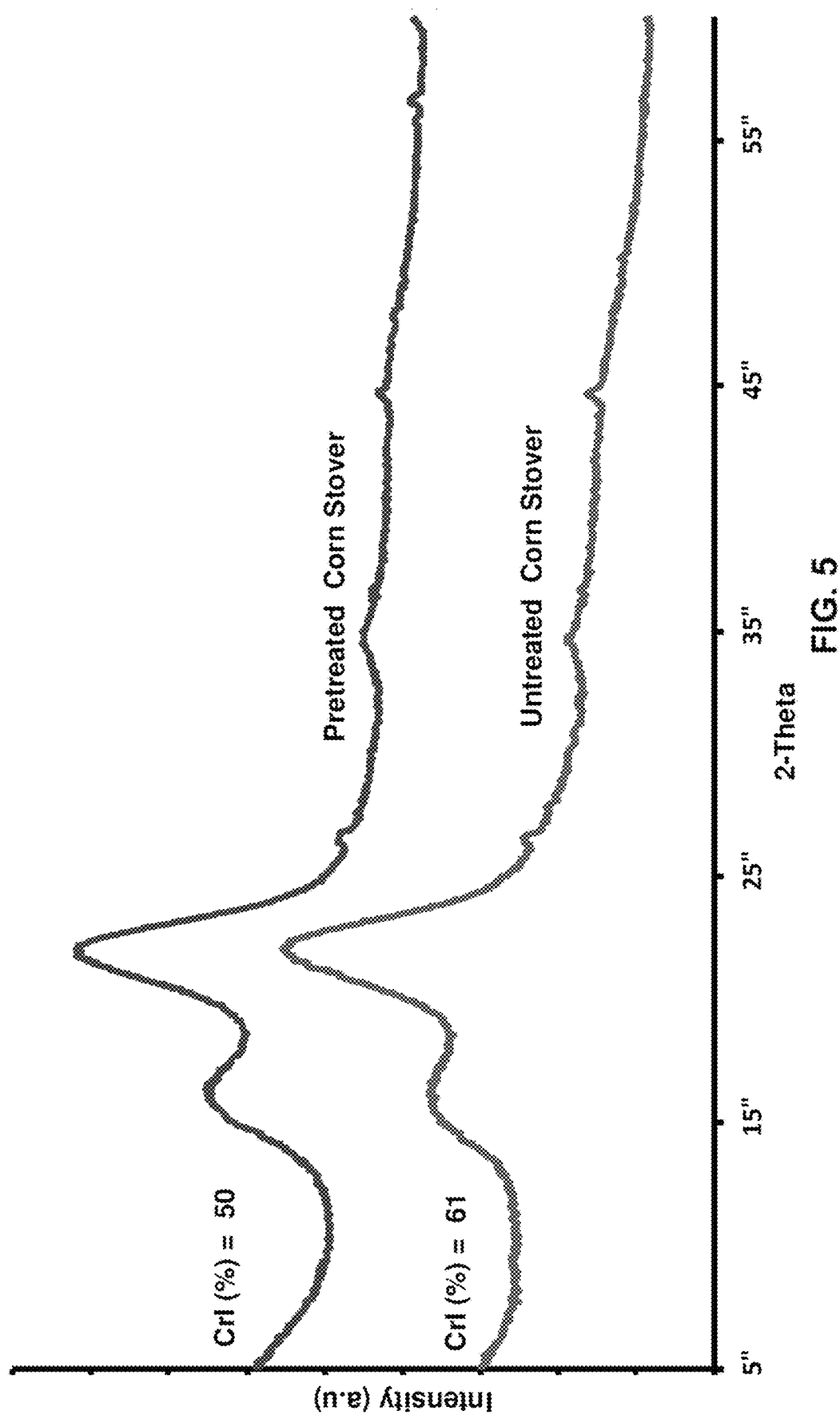
FIG. 5. X-ray diffraction patterns and CrI (%) values of untreated and pretreated corn stover by [Ch][α-Kg] (40 wt % in $H_2O$) at 120° C. for 4 h pretreatment condition.

X-ray diffraction (XRD) studies were conducted to determine the changes in the crystalline vs. non-crystalline components found in the untreated corn stover, and to monitor the structural changes in these polymers that occur during the pretreatment process. FIG. 5 shows the X-ray diffractograms of the untreated and pretreated corn stover after processing at 120° C. for 4 hrs. The diffractogram obtained from the untreated switchgrass has two major diffraction peaks at 22.5° and 15.7° 2θ, characteristic of the cellulose I polymorph that corresponds to [002] and combined [101]+[10$^-$1] lattice planes, respectively. The third small peak at 34.5° ([040] lattice plane) corresponds to ¼ of the length of one cellobiose unit and arises from ordering along the fiber direction (34, 35). The diffractogram obtained from pretreated corn stover still retains the cellulose I polymorph, with a relative decrease in the intensity of the [002] peak.

The crystallinity index (CrI) of corn stover decreased from 61% to 50% after pretreatment. This decrease in the cellulose crystallinity after pretreatment is reflected in the high saccharification efficiency observed.

Alkaline Biomass Pretreatment and Saccharification for Bioreactor Cultivation

A mixture containing 15% corn stover biomass (7 wt % moisture), 1.5% NaOH, and 83.5% water was pretreated by autoclave at 121° C. for 1 h. Following pretreatment, the biomass was wrapped in cheesecloth and dried in a laundry centrifuge to approximately 30 wt % solids. The supernatant was discarded and biomass was re-suspended and soaked in deionized (DI) water overnight after the pH was adjusted to 5.0. The pH-adjusted biomass was then centrifuged a second time to remove excess salt and moisture.

Pretreated biomass, containing 85% w/w moisture, was saccharified in 2-L IKA reactors (model LR-2.ST, IKA, USA) using commercially available enzymes CTec2 and HTec2 (Novozymes, USA). Enzymes with the following loadings were added to the reactor: 64 mg CTec2/g dry biomass and 8 mg HTec2/g dry biomass. Enzymatic saccharification was performed at 50° C. with pH in the range of 4.5 to 5.5 for 96 h. Upon completion of the saccharification reaction, the unhydrolyzed biomass was separated from the hydrolysate by centrifugation at 4000×g for 30 min. The hydrolysate was filtered with 0.7-μm and then 0.45-μm filter papers to separate any remaining particles and finally sterilized by passing through 0.2-μm filters and stored at 4° C. until use. The final hydrolysate contained 86.5 g/L of free glucose and 38.1 g/L of free xylose.

Bioreactor Cultivation Using Alkaline Hydrolysate

The seed cultures were prepared by transferring a single colony from a YPD agar plate to a 500 mL baffled flask containing 250 mL of seed medium. The seed medium consisted of 10 g/L yeast extract, 20 g/L peptone, and 20 g/L glucose. The seed was grown at 30° C., shaking at 250 rpm overnight to reach exponential growth phase. When the seed reached the exponential growth phase, 5.5% (v/v) inoculum was transferred to each bioreactor to reach an initial $OD_{600}$ of 0.6.

Bisabolene production in R. toruloides was examined in 2-L bioreactors (BIOSTAT B, Sartorius, Germany) with an extractive fermentation. Fermentation process parameters were controlled with temperature at 30° C., dissolved oxygen at 40% air saturation, and pH 5, respectively. Dissolved oxygen was controlled by adjusting the agitation rate at a constant airflow. Culture pH was controlled at 5 by automated addition of 2 M NaOH. Foaming was controlled by addition of 5% (v/v) Antifoam 204 as needed.

The batch medium in the fermenter containing SD medium had the following concentrations: 20 g/L glucose, 6.7 g/L YNB, and 0.79 g/L CSM. The feed for this reactor during fed-batch growth was 500 g/L glucose in DI water. The batch medium for the reactor containing the alkaline hydrolysate had the following concentration: 20% (v/v) corn stover alkaline hydrolysate, 6.7 g/L YNB, and 0.79 g/L CSM. The concentration of glucose and xylose in the batch medium for this reactor was 17.3 and 7.62 g/L, respectively. The feed for the fed-batch phase for this reactor was corn stover alkaline hydrolysate containing 86.5 g/L of glucose and 38.1 g/L of xylose.

Both fermenters contained 700 mL of initial batch medium and 150 mL of dodecane overlay containing 1 g/L of pentadecane as internal standard to account for evaporation of the overlay. The feed was initiated once all the sugar in the batch medium was consumed. The feed flow rate was adjusted to maintain glucose concentration in the reactors below 5 g/L. Cell growth and bisabolene production was monitored by taking 5 mL samples at predetermined time points.

Dry Cell Weight Analysis of Bioreactor Cultivations

For dry cell weight analysis 10 mL sample was removed from each reactor. After separation of the aqueous and organic phase, 5 mL sample from the aqueous phase was transferred to pre weighed falcon tubes. The cells were centrifuged at 4000×g for 10 min and supernatant was discarded. Cells were dried in a vacuum oven (Binder, Germany) at 60° C. until the weight was stable.

TABLE 1

Chemical composition of dominant components in the dry corn stover before and after pretreatment. Pretreatment conditions: 20% biomass loading, 80% [Ch][α-Kg] (40 wt % in $H_2O$), 120° C., 4 h.

| | Solid recovery/% | Glucan/ wt % | Xylan/ wt % | Lignin/ wt % |
|---|---|---|---|---|
| Untreated Corn stover | / | 38.90 ± 0.04 | 24.77 ± 0.01 | 18.42 ± 0.27 |
| Pretreated Corn stover | 60.0 | 48.35 ± 0.06 | 28.92 ± 0.05 | 13.12 ± 0.03 |

TABLE 2

Strains and plasmids used in this study.

| Plasmids | Genotypes/features | Source/ references | JBEI registry ID |
|---|---|---|---|
| Plasmids | | | |
| pGI2 | Kan$^R$ for bacteria, Nat$^R$ for yeast, binary plasmid | (30) | |
| pGI2-GPD1-BIS-Tnos | pGI2-P$_{GAPDH}$-BIS-T$_{NOS}$ | This study | JBx_065214 |
| pGI2-GPD1-ADS-Tnos | pGI2-P$_{GAPDH}$-ADS-T$_{NOS}$ | This study | JBx_065213 |
| Strains | | | |
| IFO0880 (WT) | *Rhodosporidium toruloides* strain IFO0880, mating type A2 | NBRC culture collection | |
| BIS 1-8 | IFO0880/P$_{GAPDH}$-BIS-T$_{NOS}$ | This study | JBx_065242 to JBx_065249 |
| ADS 1-8 | IFO0880/P$_{GAPDH}$-BIS-T$_{NOS}$ | This study | JBx_065232 to JBx_065239 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

All cited references are hereby each specifically incorporated by reference in their entireties.

What is claimed is:

1. A mixture of bioproducts produced by converting a mixture of depolymerized lignin aromatic compounds using a genetically modified microorganism capable of converting each depolymerized lignin aromatic compound into a bioproduct; wherein the mixture of depolymerized lignin aromatic compounds comprises:

(i) a mixture of depolymerized lignin aromatic compounds comprising the following chemical structures:

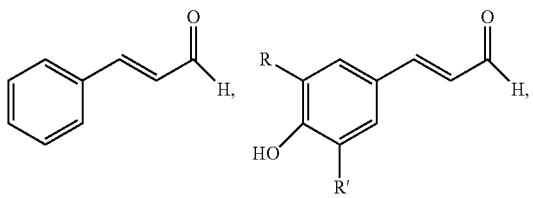

wherein R and R' are each independently —H or —OCH$_3$, and

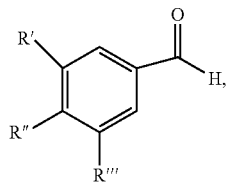

wherein R, R' and R" are each independently —H, —OH, or —OCH$_3$, (ii) a depolymerized lignin aromatic compound having the following chemical structure:

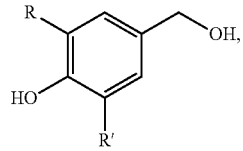

wherein R and R' are each independently —H or —OCH$_3$, (iii) a depolymerized lignin aromatic compound having the following chemical

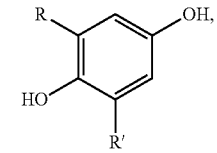

wherein R and R' are each independently —H or —OCH$_3$ and (iv) an ionic liquid.

2. A composition comprising:

(a) (i) a mixture of depolymerized lignin aromatic compounds comprising the following chemical structures:

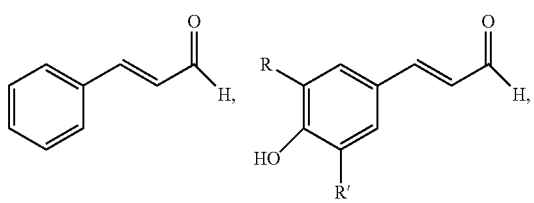

wherein R and R' are each independently —H or —OCH$_3$, and

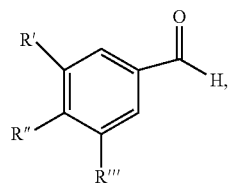

wherein R, R' and R'' are each independently —H, —OH, or —OCH$_3$, (ii) a depolymerized lignin aromatic compound having the following chemical structure:

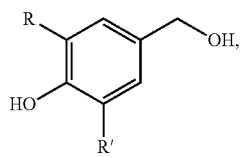

wherein R and R' are each independently —H or —OCH$_3$, and (iii) a depolymerized lignin aromatic compound having the following chemical structure:

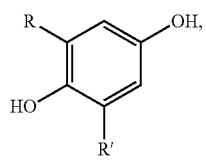

wherein R and R' are each independently —H or —OCH$_3$,
(b) a depolymerized cellulose,
(c) a depolymerized hemicellulose,
(d) a genetically modified microorganism, wherein the genetically modified microorganism is capable of converting the depolymerized lignin aromatic compound into a bioproduct, and
(e) an ionic liquid.

3. The method of claim 2, wherein the genetically modified microorganism is a fungal microorganism.

4. The method of claim 3, wherein the fungal microorganism is of the genus *Rhodotorula, Rhodosporidium,* or *Exophiala*.

5. The method of claim 4, wherein the fungal microorganism is *Rhodotorula mucilaginosa, Rhodotorula graminis,* or *Rhodotorula glutinis*.

6. The method of claim 3, wherein the fungal microorganism is *Rhodosporidium toruloides*.

7. The method of claim 3, wherein the fungal microorganism is *Exophiala alcalophila*.

8. The method of claim 2, wherein the genetically modified microorganism is a bacterial microorganism.

9. The method of claim 8, wherein the bacterial microorganism is of the genus *Delftia* or *Rhodococcus*.

10. The method of claim 9, wherein the bacterial microorganism is *Delftia acidovorans*.

11. The method of claim 9, wherein the bacterial microorganism is *Rhodococcus rhodocorus*.

12. A method of converting a depolymerized lignin aromatic compound into a bioproduct, comprising:
(a) providing a composition comprising
(i) a mixture of depolymerized lignin aromatic compounds comprising the following chemical structures:

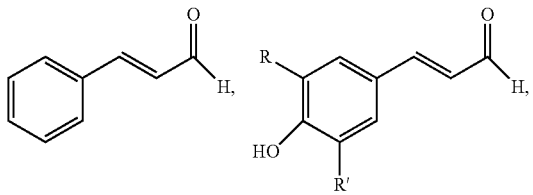

wherein R and R' are each independently —H or —OCH$_3$, and

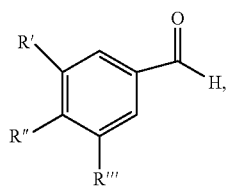

wherein R, R' and R'' are each independently —H, —OH, or —OCH$_3$, (ii) a depolymerized lignin aromatic compound having the following chemical structure:

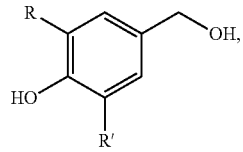

wherein R and R' are each independently —H or —OCH$_3$, (iii) a depolymerized lignin aromatic compound having the following

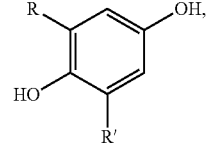

wherein R and R' are each independently —H or —OCH$_3$, and
(iv) an ionic liquid, and (b) introducing a genetically modified microorganism to the composition, wherein the genetically modified microorganism is capable of converting one of the depolymerized lignin aromatic compounds into a bioproduct;

such that the genetically modified microorganism converts a depolymerized lignin aromatic compound into the bioproduct.

13. The method of claim 1, wherein the genetically modified microorganism is a fungal microorganism.

14. The method of claim 13, wherein the fungal microorganism is of the genus *Rhodotorula, Rhodosporidium*, or *Exophiala*.

15. The method of claim 14, wherein the fungal microorganism is *Rhodotorula mucilaginosa, Rhodotorula graminis*, or *Rhodotorula glutinis*.

16. The method of claim 14, wherein the fungal microorganism is *Rhodosporidium toruloides*.

17. The method of claim 14, wherein the fungal microorganism is *Exophiala alcalophila*.

18. The method of claim 1, wherein the genetically modified microorganism is a bacterial microorganism.

19. The method of claim 18, wherein the bacterial microorganism is of the genus *Delftia* or *Rhodococcus*.

20. The method of claim 19, wherein the bacterial microorganism is *Delftia acidovorans*.

21. The method of claim 19, wherein the bacterial microorganism is *Rhodococcus rhodocorus*.

22. The method of claim 1, wherein the method further comprises contacting, prior to the providing step (a), a starting material with a depolymerization agent, wherein the starting material comprises a lignocellulosic biomass.

23. The method of claim 22, wherein the depolymerization agent is NaOH, $CuSO_4$, nitrobenzene, metal oxides, oxygen, a metal organic framework of $Cu^{2+}$ or $Fe^{3+}$, ammonium hydroxide, hydrogen peroxide, Fenton's reagent, tetralin, sodium formate, or formic acid, or imidazolium ionic liquid.

* * * * *